US012053261B2

(12) United States Patent
Fox et al.

(10) Patent No.: US 12,053,261 B2
(45) Date of Patent: Aug. 6, 2024

(54) HANDHELD CONFOCAL SCANNING OPTICAL MICROSCOPE SYSTEMS HAVING OSCILLATING MIRRORS WITH VARYING SCAN ANGLE TO ZOOM

(71) Applicant: CALIBER IMAGING & DIAGNOSTICS, INC., Rochester, NY (US)

(72) Inventors: William J. Fox, Rochester, NY (US); Scott R. Grodevant, Avon, NY (US); Christopher C. Distasio, Rochester, NY (US)

(73) Assignee: CALIBER IMAGING & DIAGNOSTICS, INC., Rochester, NY (US)

( * ) Notice: Subject to any disclaimer, the term of this patent is extended or adjusted under 35 U.S.C. 154(b) by 1025 days.

(21) Appl. No.: 16/773,400

(22) Filed: Jan. 27, 2020

(65) Prior Publication Data
US 2020/0155005 A1 May 21, 2020

Related U.S. Application Data

(60) Division of application No. 14/739,191, filed on Jun. 15, 2015, now Pat. No. 10,555,674, which is a (Continued)

(51) Int. Cl.
*A61B 5/00* (2006.01)
*A61B 90/20* (2016.01)
(Continued)

(52) U.S. Cl.
CPC .......... *A61B 5/0068* (2013.01); *A61B 5/0062* (2013.01); *A61B 5/0064* (2013.01); (Continued)

(58) Field of Classification Search
CPC ... A61B 5/0068; A61B 5/0062; A61B 5/0064; A61B 5/445; A61B 90/20; G02B 5/3083; (Continued)

(56) References Cited

U.S. PATENT DOCUMENTS 4,768,874 A  9/1988  Webb et al.
4,863,226 A  9/1989  Houpt et al.
(Continued)

FOREIGN PATENT DOCUMENTS

JP    2005017642 A  *  1/2005

OTHER PUBLICATIONS

Kim Daekeun et al., "Optical biopsy in high-speed handheld miniaturized multifocal multiphoton microscopy" Progr. Biomed. Opt. Imaging Proc. SPIE; Progress in Biomedical Optics and Imaging—Proceedings of SPIE; Multiphoton Microscopy in the Biomedical Sciences V 2005, vol. 5700, Mar. 2005, pp. 14-22, XP002403958.
(Continued)

*Primary Examiner* — Serkan Akar
(74) *Attorney, Agent, or Firm* — KENNETH J. LUKACHER LAW GROUP; Kenneth J. LuKacher

(57) ABSTRACT

A confocal microscope having a scanning head in the form of a hand piece (102) which may be placed at selected locations on the body of a patient. A laser beam is scanned in orthogonal (horizontal and vertical) directions by scanners (128, 130) which drive scan mirrors (128a, 130a), which are closely adjacent to each other. The optics include an objective lens (138) and a single telescope lens (132, 134). The telescope provides sufficient magnification to overfill the entrance pupil of the objective lens (138) over the entire scan angle produced by the scan mirrors (128a, 130a). The telescope images the entrance pupil of the objective in the beam path between the mirrors of the scanners. Scanner (128) represents a pulse driven resonant (Continued)

scanner (7). The pulse duration is controlled to vary the scan angle and obtain dynamic, electronic image zooming without changing the positional relationship of the telescope lenses.

18 Claims, 19 Drawing Sheets

Related U.S. Application Data continuation of application No. 11/920,195, filed as application No. PCT/US2006/018777 on May 12, 2006, now Pat. No. 9,055,867.

(60) Provisional application No. 60/680,384, filed on May 12, 2005.

(51) Int. Cl.
 *G02B 5/30* (2006.01)
 *G02B 21/00* (2006.01)

(52) U.S. Cl.
 CPC .............. *A61B 5/445* (2013.01); *A61B 90/20* (2016.02); *G02B 5/3083* (2013.01); *G02B 21/0008* (2013.01); *G02B 21/0028* (2013.01); *G02B 21/0048* (2013.01); *G02B 21/0068* (2013.01); *G02B 21/0072* (2013.01); *G02B 21/008* (2013.01)

(58) Field of Classification Search
 CPC ............ G02B 21/0008; G02B 21/0028; G02B 21/0048; G02B 21/0068; G02B 21/0072; G02B 21/008
 See application file for complete search history.

(56) References Cited

U.S. PATENT DOCUMENTS

| | | | |
|---|---|---|---|
| 4,991,953 A | 2/1991 | Pflibsen et al. | |
| 5,048,904 A | 9/1991 | Montagu | |
| 5,107,422 A | 4/1992 | Kamentsky et al. | |
| 5,120,953 A | 6/1992 | Harris | |
| 5,121,138 A | 6/1992 | Schermer et al. | |
| 5,122,653 A | 6/1992 | Ohki | |
| 5,225,923 A | 7/1993 | Montagu | |
| 5,347,124 A | 9/1994 | Narukawa et al. | |
| 5,532,874 A | 7/1996 | Stein | |
| 5,719,700 A | 2/1998 | Corcuff et al. | |
| 5,788,639 A | 8/1998 | Zavislan et al. | |
| 5,880,880 A | 3/1999 | Anderson et al. | |
| 5,995,867 A | 11/1999 | Zavislan et al. | |
| 6,032,071 A | 2/2000 | Binder | |
| 6,069,690 A | 5/2000 | Xu et al. | |
| 6,134,009 A | 10/2000 | Zavislan | |
| 6,151,127 A | 11/2000 | Kempe | |
| 6,263,233 B1 | 7/2001 | Zavislan et al. | |
| 6,282,020 B1 | 8/2001 | Ogino | |
| 6,304,373 B1 | 10/2001 | Zavislan | |
| 6,429,968 B1 | 8/2002 | Carver | |
| 6,434,416 B1 | 8/2002 | Mizoguchi et al. | |
| 6,580,554 B2 | 6/2003 | Engelhardt et al. | |
| 6,703,603 B2 | 3/2004 | Tohyama et al. | |
| 6,745,067 B1 | 6/2004 | Zavislan et al. | |
| 6,769,769 B2 | 8/2004 | Podoleanu et al. | |
| 6,791,698 B2 | 9/2004 | Doemens et al. | |
| 6,927,860 B2 | 8/2005 | Podoleanu et al. | |
| 6,991,939 B2 | 1/2006 | Walt et al. | |
| 7,047,064 B1 | 5/2006 | Zavislan et al. | |
| D523,883 S | 6/2006 | Distasio et al. | |
| 7,190,329 B2 | 3/2007 | Lewis et al. | |
| 7,236,251 B2 | 6/2007 | Takaoka | |
| 7,394,592 B2 | 7/2008 | Fox et al. | |
| 2003/0032204 A1* | 2/2003 | Walt | G21K 1/006 435/7.1 |
| 2004/0036838 A1 | 2/2004 | Podoleanu et al. | |
| 2004/0085261 A1 | 5/2004 | Lewis et al. | |
| 2004/0207811 A1* | 10/2004 | Elsner | A61B 3/1025 351/205 |
| 2004/0233457 A1 | 11/2004 | Podoleanu et al. | |

OTHER PUBLICATIONS

Extended European Search Report, European Patent Application No. 06770376.9, dated Apr. 3, 2014.

Ernst H.K. Stelzer, Considerations on the Intermediate Optical System in Confocal Microscopes, Handbook of Biological Confocal Microscopy, ed. James Pawley, pp. 83-92, 1989.

P. M. Delaney et al., Fiberoptics in Confocal Microscopy, Handbook of Biological Confocal Microscopy, ed. James Pawley, pp. 515-523, 1995.

T. Wilson, The Role of the Pinhole in Confocal Imaging Systems, Handbook of Biological Confocal Microscopy, ed. James Pawley, pp. 99-113, 1989.

* cited by examiner

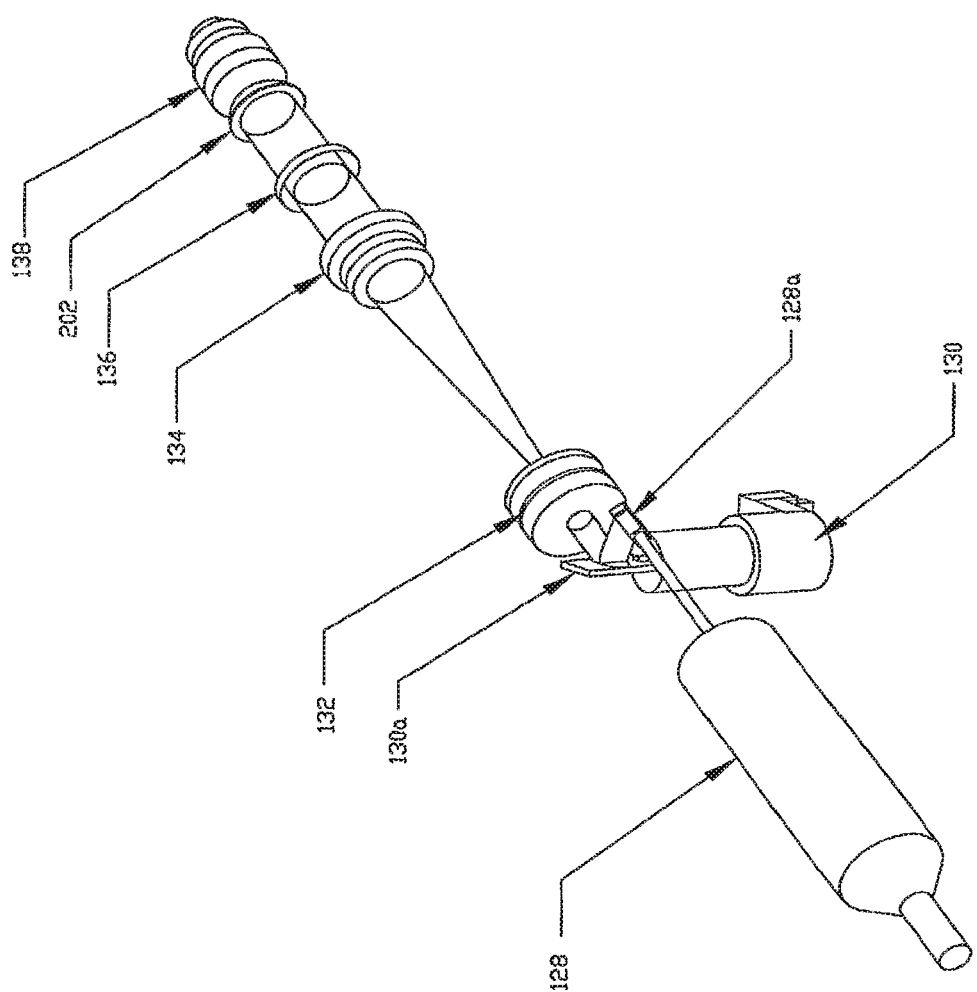

HANDHELD CONFOCAL SCANNING OPTICAL MICROSCOPE SYSTEMS HAVING OSCILLATING MIRRORS WITH VARYING SCAN ANGLE TO ZOOM

This application is a divisional of U.S. patent application Ser. No. 14/739,191, filed Jun. 15, 2015, now U.S. Pat. No. 10,555,674, which is a continuation of U.S. patent application Ser. No. 11/920,195, filed Nov. 9, 2007, now U.S. Pat. No. 9,055,867, which is a 371 of International Patent Application No. PCT/US06/18777, filed May 12, 2006, which claims priority to U.S. Provisional Patent Application Ser. No. 60/680,384, filed May 12, 2005, which is incorporated by reference.

DESCRIPTION

The present invention relates to confocal microscopes for the imaging of selected locations on the body of a patient by incorporating the imaging head in a hand piece adapted to be placed at such locations by manipulation thereof. The handheld confocal microscope provided by the invention is especially useful for cellular imaging of the skin of a patient at such selected locations as well as for the imaging of other living tissue and biological processes.

It is the principal feature of the invention to provide a scanning microscope having optical components and electro-mechanical scanning components in compactly organized relationships so as to provide an imaging head in the form of a hand piece sufficiently small and light in weight to be manipulated by the microscope operator.

It is a further feature of the invention to provide scanning microscope optics by which a scanning beam is projected to be incident on the locations being imaged and is returned from such locations, and in which optics the number of optical components is minimized to enable compact organization thereof in a hand piece.

It is a still further feature of the invention to provide compact optics which fills an objective lens of a scanning microscope sufficiently to accommodate the scanning beam over its entire, maximum scan angle.

It is a still further feature of the invention to provide compact optics which maintains performance of the optical system of a scanning microscope, particularly the numerical aperture (NA) of the objective, so as to facilitate resolution of the image obtained by the microscope over the full field of the image and enabling sections of the specimen being imaged to be closely adjacent to each other.

It is a still further feature of the invention to provide a scanning system adapted to be compactly configured so as to be suitable for use in a hand piece enclosing the optics and electronics for implementing a confocal laser scanning microscope by utilizing, for at least one of the scanning mechanisms thereof, a resonant scanner which is efficiently driven for minimizing heat generation and dissipation requirements.

It is a still further feature of the invention to provide an improved resonant scanning system, which may be adapted for use in a compact hand held confocal laser scanning microscope, which is pulse driven and has frequency and phase control so as to maintain operation at constant phase and at a frequency where the scanner of the scanning system is resonant.

Confocal laser scanning microscopes have been provided which have confocal imaging systems suitable for imaging of skin and other cellular tissues, and reference may be had to Zavislan and Eastman, U.S. Pat. Nos. 5,788,639 and 6,263,233, issued Aug. 4, 1988 and Jul. 17, 2001, respectively, for confocal microscopes which may be handheld. Confocal microscopes having resonant scanners have also been described in Montague, U.S. Pat. No. 5,225,923, issued Jul. 6, 1993 and control systems for resonant scanners utilizing analog drivers in a phase controlled loop have been described in Schermer et al., U.S. Pat. No. 5,121,138, issued Jun. 9, 1992.

Where precise high resolution imaging is required, linear scanning has been provided with a polygon scanner or galvanometer scanners for horizontal and vertical deflection and separate optics is needed between the scanners themselves and from the last scanner to the objective lens of the microscope. Such optics and polygon scanning facilities are however, not easily adaptable for incorporation in a sufficiently compact configuration for use in a handheld confocal microscope. Reference may be had to the following patents and publication for such confocal laser scanning microscopes having polygon scanners, Anderson et al. U.S. Pat. No. 5,880,880, issued Mar. 9, 1999, and International Publication No. WO2004/104645, published Dec. 2, 2004.

It has been discovered, in accordance with the invention, that compact configuration suitable for handheld applications may be facilitated by the use of scanners from which the laser beam is deflected in orthogonal (say horizontal and vertical) directions which are spaced closely adjacent to each other. The beam is relayed by a telescope lens, which may have two lenses, spaced between the scanners and the objective lens of the microscope. Such a single telescope, if focused on one of the scanners or the other, does not maintain a constant numerical aperture at the entrance pupil of the objective lens. Instead the beam moves past the entrance pupil (the aperture of the lens) and illumination may not reach the desired location of the specimen being imaged. The beam may be considered to have walked off the entrance aperture or pupil of the objective at the limits of the scan angle (the deflection) of the beam. In accordance with the invention, both the full entrance pupil of the objective is illuminated over the entire scan angle, and the numeral aperture (NA) of the objective is maintained, thereby maintaining the performance of the scanning system. To this end, the telescope uses a first lens which images or focuses at a position between the scanning mirrors of the scanners. Preferably midway between the mirrors along the line between their deflection axes, but closer to one mirror than the other, for example, if the scanning mirrors are not symmetric about their axes. The second lens of the telescope, which is preferably of longer focal length than the first lens thereof, provides with the first lens sufficient magnification to overfill the entrance pupil of the objective over the entire scan angle (the deflection) of both scanning mirrors. The loss of laser power is not significant, since the laser beam may be provided with sufficient power for imaging through the entire scan, even though some power is lost due to the overfill condition of the objective entrance pupil. Accordingly, the performance of the confocal scanning microscope is obtained not withstanding the compact configuration and minimization of optical components in the optics of the microscope.

The resonant scanner is especially adapted for use in a compact configuration and is more adapted for such configuration than a polygon scanner as discussed above. However, resonant scanners tend to drift off their natural (resonant) frequency. Analog frequency control loops have been provided to compensate such drifting. See U.S. Pat. No. 5,121,138 referenced above. Drift usually occurs with temperature increases and temperature increases are aggravated since the resonant scanner drive, under analog control, is inefficient and utilizes power which aggravates heating of the scanner. The present invention provides power efficient, digital control of a resonant scanner. The scanner is driven with pulses which can be generated efficiently and maintains both operation at scanner's resonant frequency and drive at constant phase angle. The pulse duration may be selected thereby selecting the scan angle and enabling different fields of view to be scanned, thereby providing optoelectronic controlled zooming of the image; that is, a display of smaller and larger fields of view with the same resolution.

While a hand held confocal laser scanning microscope application for the resonant scanner control system is specifically provided by the invention, the resonant scanner control system may be employed for other scanning applications than in a handheld confocal laser scanning microscope and all such applications are within the scope of the invention.

Briefly, commercially available resonant scanners may be suitable for use in implementing this invention. For example, the CRS series manufactured by GSI Lumonics; 500 Arsenal Street, Watertown, Massachusetts 02472 USA, is a suitable resonant scanner. Such a resonant scanner consists of a mirror mounted to a torsional element that is magnetically coupled to both a drive and sense coil. Typically the mirror is used to deflect a laser for the purpose of creating a single axis reciprocating scan or one axis of a multi-axis raster pattern. The amplitude of mirror oscillation determines reflected beam angle, also commonly called scan angle. Due to the nature of the optical system of the confocal microscope, this scan angle translates into field of view. Thus this invention scan angle control provides for optoelectronic, dynamically varying field of view of the scanned image.

Resonant scanners are specifically constructed so as to minimize energy losses and, as a result, are high-Q (quality factor) devices. Q-factors of 500 to 1000 are typical. Because their Q's are high, their operating frequency range is very small as defined by Equation 1:

$$Q = \frac{f_o}{BW} \quad (1)$$

With Q ranging from 500-1000, and $F_o$ (the system's resonant or natural frequency) near 8 KHz system bandwidth (BW) is about ten hertz (8-16 Hz), in a commercial resonant scanner such as referred to above.

The scanner's resonant frequency drifts, usually due to heat generated by the tortional elements as the device operates. The resonant scanner system of this invention continuously monitors and adjusts operating frequency, and avoids reduction of scan angle (decay of scan angle) as the resonant frequency drifts away from the drive frequency.

A common method of resonant scanner control is constructed using a phase-shift oscillator using the drive coil. See for example, U.S. Pat. No. 5,121,138, issued Jun. 9, 1992 and U.S. Pat. No. 5,225,923, issued Jul. 6, 1993, referenced above. A drawback of phase shift oscillator control is that its power driver stage (that supplies power to the scanner coil) operates in its linear region. This results in high power dissipation which causes undesirable heating. Although this can make design of a scanning microscope sufficiently small to be handheld, it is difficult to accomplish. It is thus a feature of this invention to drive the resonant scanner by pulsing the coil driver, preferably with saturated switches, thereby eliminating wasted power, and reducing power dissipation and heating, without sacrificing operation performance. The resonant scanner then can be used in confined spaces, such as in a confocal microscope hand piece, where dissipation of heat capability is limited.

Heretofore confocal microscopes have used rotating polygons for fast scanning. See for example International Publication No. WO 2004/104645, published Dec. 2, 2004, entitled, "Confocal Microscope for Imaging of Selected Locations of the Body of a Patient" referenced above. Two major disadvantages of a resonant scanning system compared to a rotating polygon stem from the scanner's oscillatory motion. Resonant scanners by their very nature, oscillate back and forth. Rotational speed, and hence reflected beam speed, by virtue of the resonant scanner's high Q are very near sinusoidal. Because of this sinusoidal movement, uniformly timed samples are not linear in a spatial sense. A sampling clock sinusoidally modulated in time of occurrence of the clock pulses is needed to provide spatially equidistant samples; referred to herein as sample clock linearization. It is a feature of this invention to provide an improved system for generating this clock.

A second disadvantage of a resonant scanning system stems from the forward and reverse beam movement which requires correlating forward- and reverse-scanned data or discarding data collected in one or the other direction. In accordance with a presently preferred embodiment of the invention data in the reverse-scanned direction is not used. It is within the scope of the invention to use both forward- and reversed-scanned data, which is correlated so as to provide scanned data for successive lines in our image frame. Correlating forward- and reverse-scanned data doubles frame rate, significantly reducing artifacts for example visual movement artifacts between the confocal microscope and tissue sample.

It is a further feature of the present invention to provide a resonant scanning system using raster generation with the ability to dynamically control image magnification (e.g., by controlling field of view) thereby affording optoelectronic zooming of the image. The invention provides for dynamically controlling scan angle and thus field of view, and therefore variable zooming of the image. Heretofore, especially where rotating polygon scanning was used, zooming capability required movable lenses or a rotatable turret with separate lens sets for each magnification of the imaged location. In accordance with a presently preferred embodiment of the resonant scanning system according to the invention, an electronic waveform is applied to the drive coil whose frequency is initially very near, but greater than, the specified resonant frequency of the scanner (typically the frequency due to the moving torsional elements and their mass at standard room temperature). This is 8 KHz in the commercial resonant scanner mentioned above. This waveform causes the torsional element, and hence the scanning mirror, to oscillate at the applied frequency. The sense coil monitors the resulting motion of the scanner. The signal from the sense coil is proportional to the scanner's instantaneous velocity. Integrating the signal to obtain the position data has several drawbacks such as the integrator's unknown state during non-scanning periods, and dealing with the integration constant. Instead of an integrator, a low-pass filter is used to produce the negative of the position signal, which can be amplified and inverted to derive the scanner's instantaneous position. The low-pass filter is preferred since it is less complex than an integrator and does not produce integration errors.

This derived position signal serves as the basis for generating a sinusoidally modulated (in time of occurrence) sampling clock. By sampling fastest when the beam is in the center of its scan (and moving fastest) and more slowly as the beam reaches its movement extremes, digitized video samples (pixels) correspond to generally spatially equidistant points along the scan.

The velocity signal is also converted to a digital waveform named SOS (start-of-scan) using an analog comparator which trips when the velocity signal is above a referenced potential, such as ground (zero voltage). The comparator's transition point, when its output switches from low to high, marks the beginning of the forward beam scan and the start of forward video data collection. This signal provides for video data synchronization and display, and also for scanner frequency control. The original signal velocity may be converted into a wave form which provides a start of scan pulse as the velocity signal changes from high to low (second half of each cycle). The vertical scan may be synchronized with each half cycle to provide successive scans in opposite direction, thereby increasing the data collection rate.

The phase of SOS relative to the driving pulse is measured by the control system. The control system adjusts the drive waveform (pulse) frequency based on this measured phase value so as to maintain constant phase. By choosing the constant phase operating point to be 90°, the system is operated at its resonant frequency. By operating the scanner at resonance or very near resonance (accounting for control loop error), the resulting scan angle is maximized for any input power level, therefore the scanner operates at its most efficient frequency.

The drive waveform is preferably of a series of positive and negative voltage pulses being alternately applied every half-cycle thereof. Then, the resonant scanner's oscillation center is the same as its resting position. While unipolar pulses may be used to drive the scanner, this is not preferred since the center of scan may be displaced from its resting center of the scanner, thereby complicating optical system alignment, when the scanner is at its resting center.

Further, the duty-cycle (pulse durations) of the drive waveform is varied independently of frequency to control peak scanner position (e.g., scan angle), thus accomplishing dynamic magnification (zoom) of the raster scanned image. Alternately, the drive pulse amplitude can be varied to control scan angle Thus, the pulse duration of the pulse driven resonant scanner is controlled to vary the scan angle and obtain dynamic, electronic image zooming without changing the positional relationship of the telescope lenses. Pulse drive also minimizes electrical power requirements and heating so as to facilitate installation of the scanning system and optics in a confined space in the hand piece. A dual variable control loop controls the resonant scanner drive pulse frequency and phase to maintain resonant scanning rates and scan angle constant during the operation of the microscope.

As the description proceeds the electronic circuitry and software programming which may be used to implement the above-described system will become more apparent. Also becoming more apparent will be a further feature of the invention in providing circuitry which can be minimized relative to cost and component count and can be reflected in the cost of a confocal microscope system embodying the invention.

BRIEF DESCRIPTIONS OF THE DRAWINGS

The foregoing objects, features and advantages of the invention will become more apparent from a reading of the following description in connection with the accompanying drawings, in which.

Figure 20A:
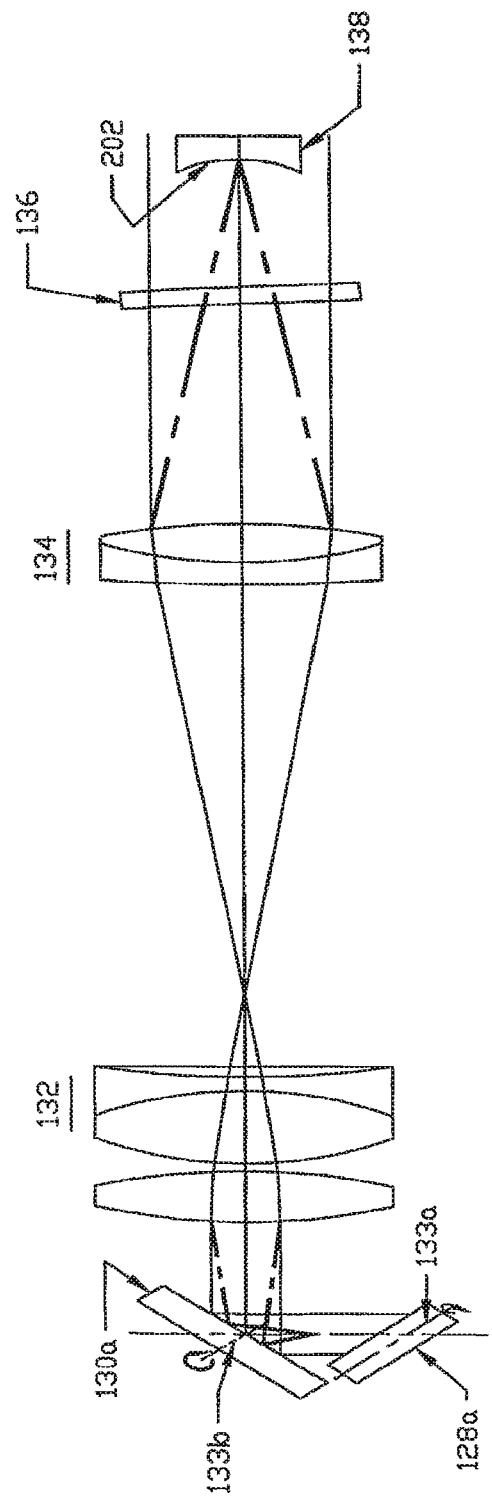
Figure 20B:
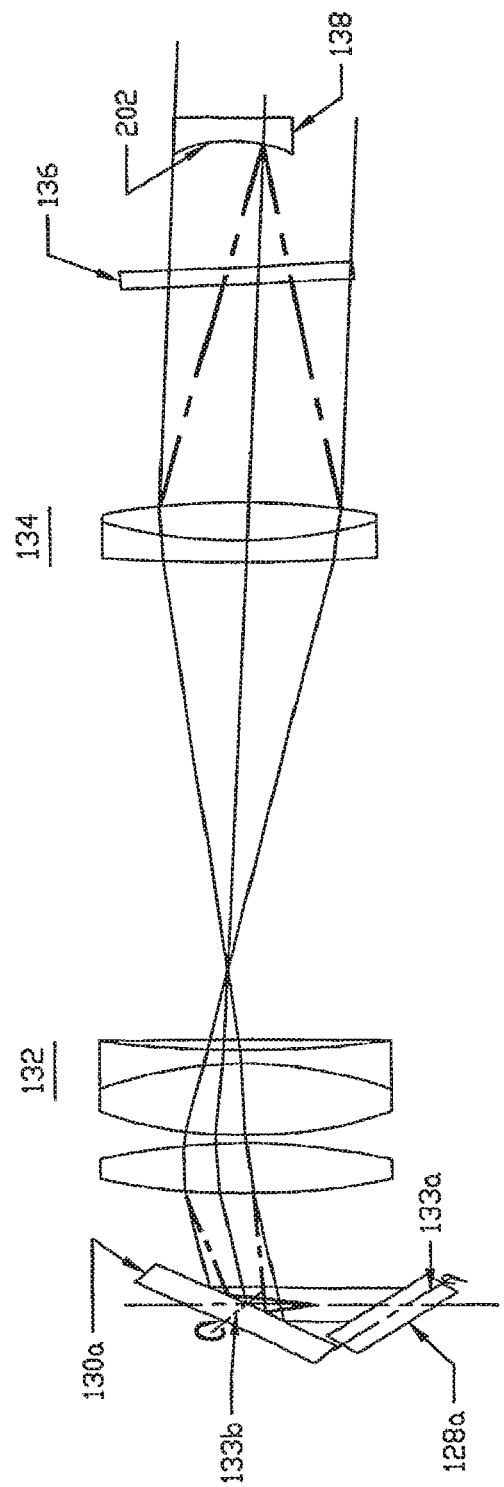

FIG. 19 is a perspective view of the scanners and the optics between the scanner and the microscope objective, showing the beam path and diameters; and FIGS. 20A and 20B are schematic views of the scanner, mirrors and optics showing the operation of the optics in providing an overfill condition of the objective entrance pupil so that the entrance pupil is filled over the entire scan angle and the NA of the objective is maintained.

DETAILED DESCRIPTION OF THE INVENTION

Figure 12:
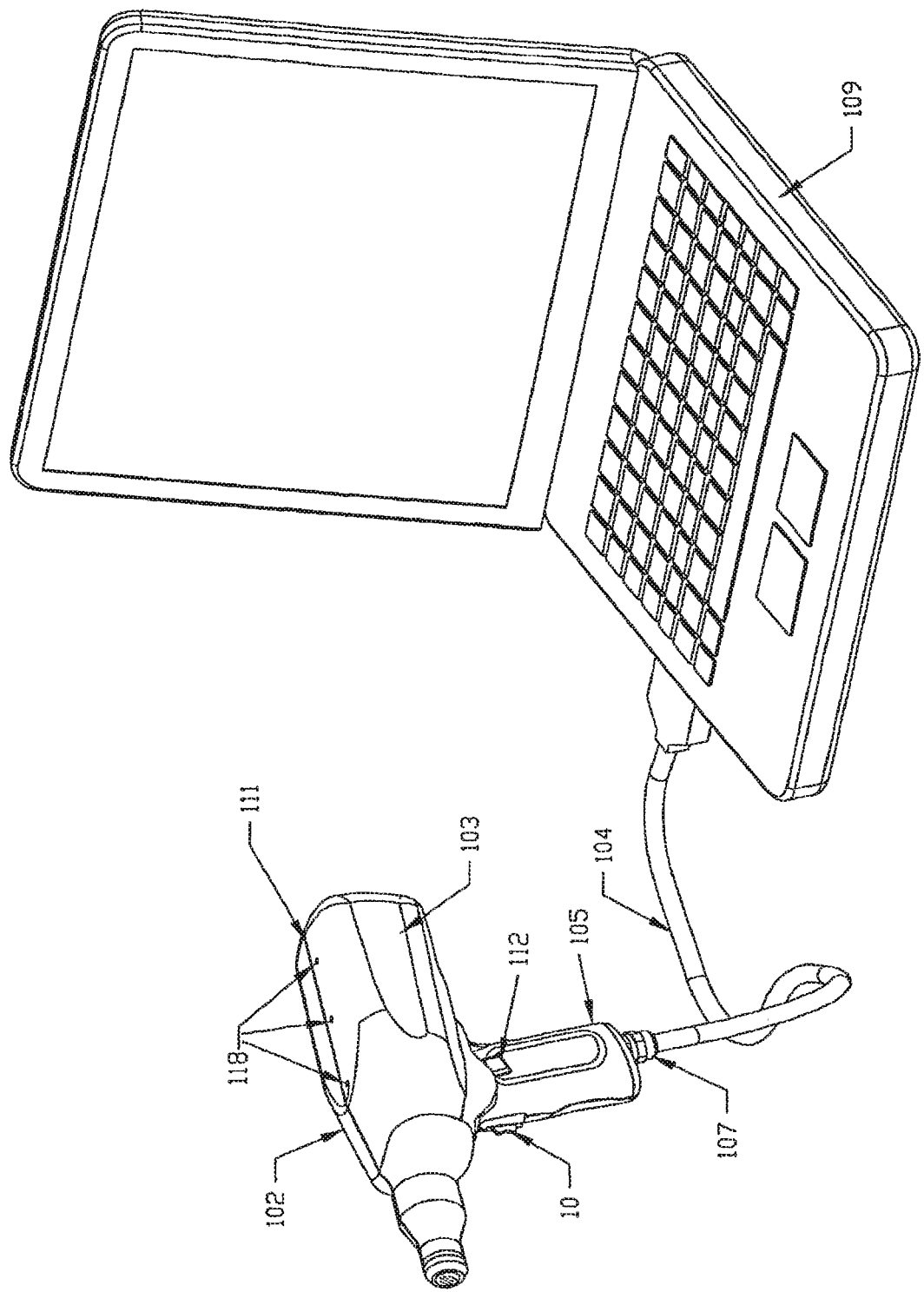
FIG. 12 is a perspective view of the handheld laser scanning confocal microscope system including the imaging head in a gun shaped hand piece and a portable personal computer interconnected by a cable; the hand piece being shown from the right side thereof.
Figure 13:
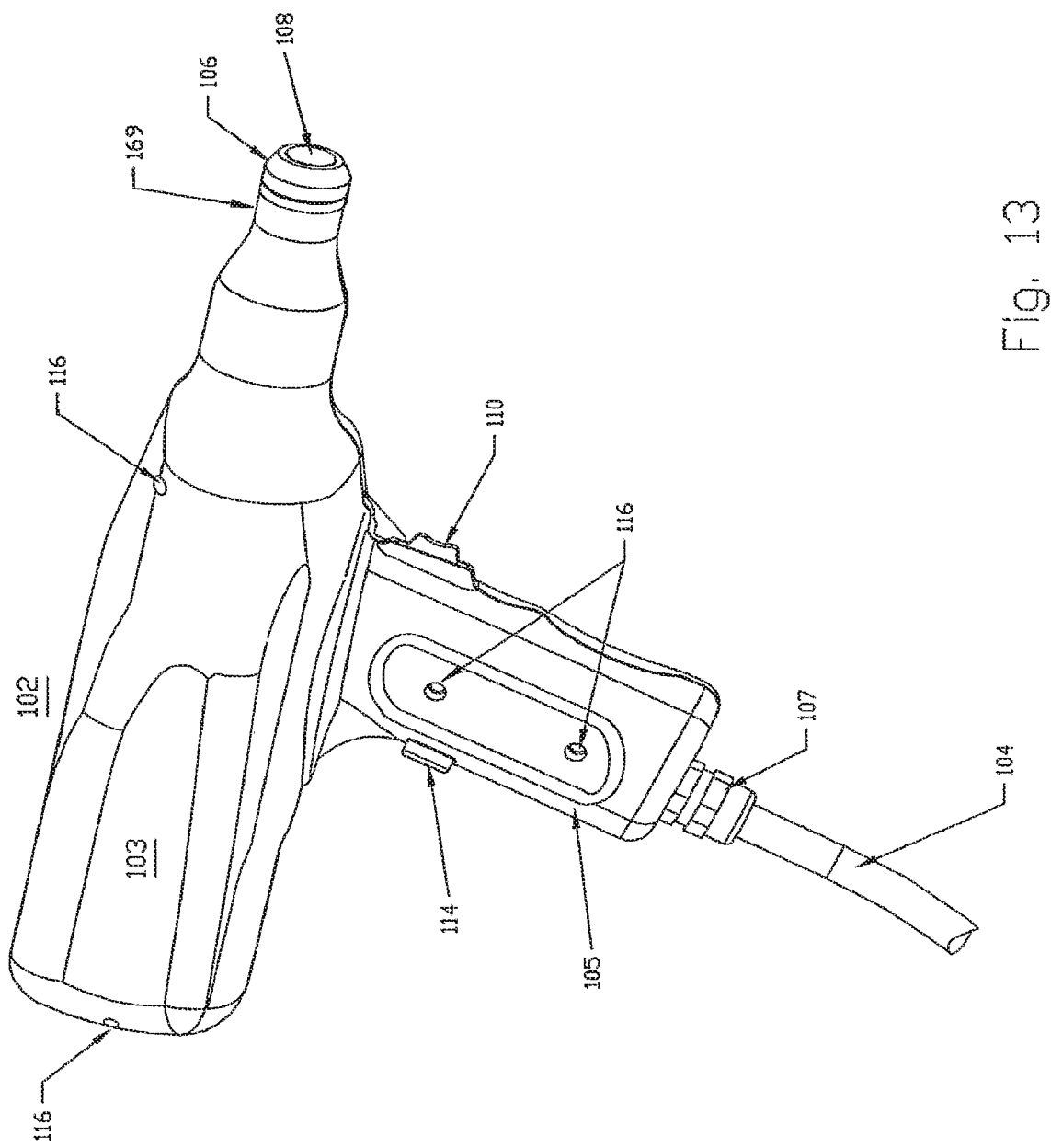
FIG. 13 is a perspective view of the hand piece shown in FIG. 12 taken from the left side thereof.

Referring first to FIGS. 12 and 13, there is shown a hand piece 102 of a hand held, laser scanning confocal microscope. This microscope is used to obtain images suitable for dermatological, pathological examination of the surface or internally of lesions on a patient's skin, when the window 108 in a ring 106 located at the end of nose piece 169 of the hand piece 102 is placed against the skin of the patient. Further information on the use of a confocal microscope in pathological and dermatological applications may be obtained from the above referenced Zavislan et al. and Anderson patents and the international publication.

The hand piece 102 has a body section 103 which may be four to nine inches long from the window 108 to the back end of the body 103. The body is generally square in cross sections which may be four by four inches. The hand piece 102 may be manipulated with the aid of a handle 105. A cable 104 connects the hand piece 102 via a connector 107 at the base of the handle 105 to a commercial personal computer (PC) 109, shown for example as being of the laptop type, but other type of computer may be used, such as a desktop type. The images obtained by the microscope in the hand piece 102 are processed in the computer 109 and displayed on the computer's screen or display.

Imaging may be controlled with a trigger switch 110 which selects laser power and focuses the microscope at a desired location on or within the lesion in the skin or other specimen which is to be imaged. Laser power and focus may be selected by toggling the switch 110 up and down. Another push button switch 112 is depressed for image capture, when a display is required on the screen on the PC 109. Another switch 114 may be operated by the palm of the hand of the operator and provides an interlock function for safety purposes, such that the laser in the microscope can only be maintained on and in beam producing operation when the switch 114 is depressed.

The exterior of the hand piece 102 is a case made up of two shells which are assembled along a parting line 111. The handle 105 may be extensions of the shells which form the case of the hand piece 102. The shells may be assembled together into the unitary case of the hand piece 102 by fasteners (screws or nuts and bolts) which are captured in apertured internal supports 113 and 119 (see FIG. 16) in the microscope structure internal of the case formed by the shells. The internal structure is also captured by screws extending from openings providing mounting positions 116. The case shell parts may also have apertured bosses 118 which receive mounting screws for holding the shells of the case together along the parting line 111.

The cable 104 carries the data representing the images which is processed in the PC 109. The cable 104 also provides power from the PC 109 to operate the electric circuits and electro mechanical actuators and scanners in the hand piece 102. If it is desired to eliminate the tethering of the hand piece via the cable 104, a pack 120 (shown in FIG. 14) containing batteries for powering the microscope in the hand piece may be used. This pack may also contain an optical or infrared data link which carries image data to the PC in a manner similar to other optical (e.g., infrared) data links used for remote control of electronic and telecommunication devices.

The structural configuration of the confocal microscope, including the internals in the case thereof will be discussed in connection with FIGS. 16 through 18. In order to facilitate the understanding of the structural configuration, and the features of the optical arrangement provided by the invention, which enable the microscope to be configured and packaged in an efficiently small space for hand held operation, particular reference may be had to FIGS. 15, 19, 20A and 20B.

Figure 1:
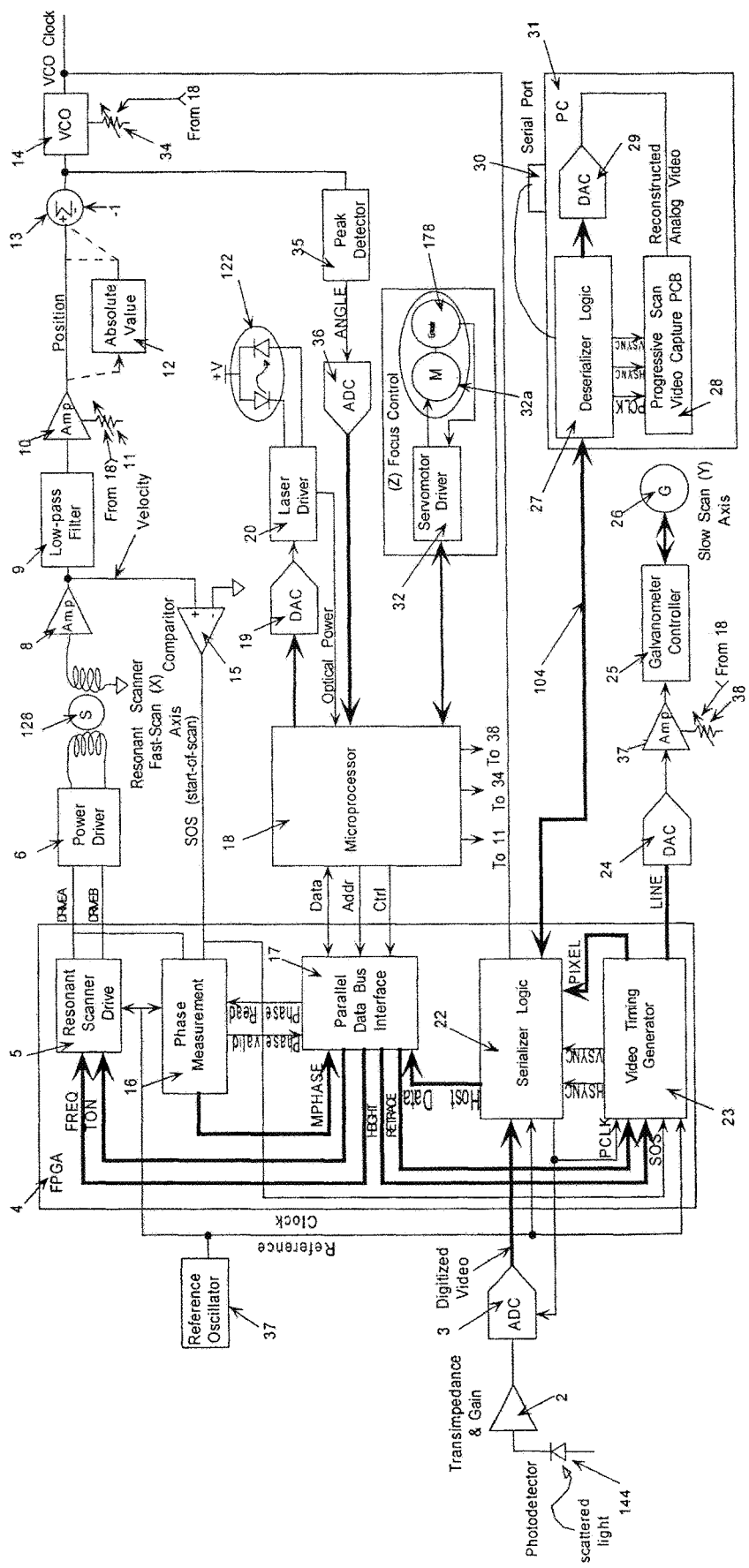
FIG. 1 is a block diagram of the electrical system of a confocal laser-scanning microscope having a scanning system including a resonant scanner, embodying the invention.
Figure 15:
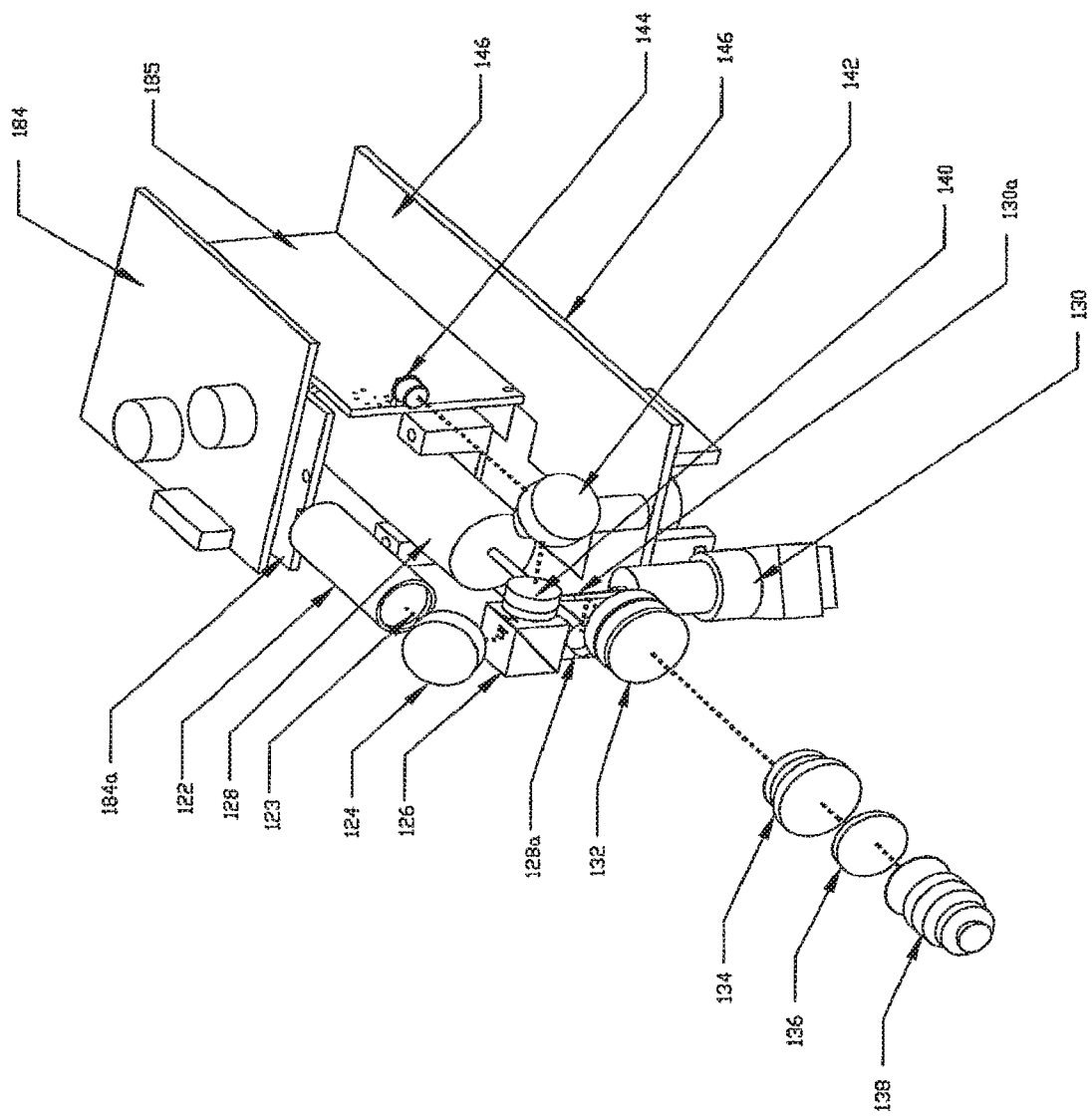
FIG. 15 is a schematic perspective view illustrating the internals (the optics including the scanners and boards carrying electronic circuits of the microscope which are contained in the hand piece)

As shown in FIG. 15, a laser 122, preferably a laser diode which is associated with an optodetector for monitoring laser power as shown in FIG. 1, provides a linearly polarized beam 123. The beam is reflected by a turning mirror 124 and passes through a polarizing beamsplitter 126. A resonant scanner 128 presents its scanning mirror 128a to the beam. This mirror 128a provides the fast or horizontal line scans in the raster being scanned. The slow or vertical scan and retrace are provided by a galvanometer 130 having a scanning mirror 130a. The scan beam from the resonant scanner mirror 128a is incident on the galvanometer or galvomirror 130a. The axes 133a and 133b of oscillation of these mirrors 128a and 130a (see FIGS. 20A and B) are orthogonal (perpendicular) to each other. Moreover, the mirrors are closely adjacent thereby contributing to the compact configuration of the confocal microscope. The separation distances are approximately a minimum separation distances to provide clearance between the mirrors as they scan. The close relationship of the mirrors will be further apparent in FIGS. 19, 20A and 20B.

A single telescope lens having two lens elements 132 and 134 relays the scanning beam to an objective 138 via a quarter wave plate shifter 136. The relay lens elements 132 and 134 are compound lenses made up of convex and concave lens elements (see FIGS. 20A and 20B) such as are conventionally in telescope lenses. The wave plate 136 may be tilted to the optical axis of the telescope and objective, to reduce back reflection, as will be more apparent in FIGS. 20A and 20B. The quarter wave shift provided by the plate 136 rotates the polarization of the beam to facilitate separation of the return light in the beamsplitter 126.

The return light from the tissue passes through the objective 138, the wave plate 136, the telescope lens 132 and 134, and the scanning mirrors 130a and 128a. The return light is descanned at the mirrors 128a and 130a into a stationary beam and enters the polarizing beamsplitter 126. From the beamsplitter 126, the return light is focused by a focusing lens 140 to a small aperture provided by a pinhole (or a lens) in front of photo detector 144. Preferably, rather than a pinhole, the active area of photo detector 144 can be equal to the aperture size. The beam from the focusing lens 140 to the photo detector 144 is turned by a mirror 142.

The laser 122 and the mirrors 124 and 142 are all adjustable. The laser 122 can be tilted in orthogonal directions (up-down and sidewise) and the mirror 124 is movable laterally along the direction of the laser beam. The adjustability is provided to keep the beam in alignment with the scanner mirrors 128a and 130a. The mirror 142 can be tilted in orthogonal directions (also up-down and sidewise) to keep the return beam aligned with the photo detector 144. The objective lens 138 may move along the optical axis (the Z axis) of the optical system so as to focus the beam at selected locations at the surface or the internal sections of the specimen to be imaged.

As shown in FIG. 19, the telescope lenses 132 and 134 are magnifying optics having a focus between the lenses and which collimate the light passing outwardly from the telescope. The first telescope lens 132 (nearest to the scanning mirrors 128a and 130a) collects the light over the entire scanning angle. However the scanning beam has a tendency to walk over the objective entrance pupil 202. It is a feature of the invention to facilitate a compact configuration for the microscope by means of a single telescope lens without cutting off the scanning beam at the extremes of its scan. Another feature accomplished by the invention is to maintain the numerical aperture (NA) of the objective lens over the entire scan, by utilizing the entire entrance pupil of the objective 138 over the entire scan angle of the scanning beam.

As shown in FIGS. 20A and 20B, the telescope lenses 132 and 134 provide sufficient magnification by virtue of their focal lengths so as to overfill the objective entry pupil 202. Lens 132 is closest to the scanning mirrors 128a and 130a, while lens 134 is closest to the objective 138. The focal length of lens 132 is less than the focal length of lens 134, and the focal lengths of lenses 132 and 134 are in a ratio to provide the magnification of the telescope. This overfilled condition is maintained even at the maximum scan angle (for example 8° in each sense of rotation about the axes of rotation 133a of the galvomirror 128a and 133b of the resonant scanner mirror 130a). FIG. 20A shows the scanning beam at center of the scan. FIG. 20B shows that, even at the maximum scan angle, the objective entrance pupil 202 stays filled. The beam is then collected by the objective over its entire entrance pupil. Since the entire entrance pupil is used, the numeral aperture (NA) of the objective is retained. The higher the NA the greater the resolution of the objective, and the closer which focused spots in the plane of the imaged specimen can be, as well as maintaining the vertical section thickness.

Also as shown in FIGS. 20A and 20B, in order to minimize the amount of walking of the beam at the entrance pupil 202 of the objective 138, over the scan angle, the first lens 132 has a focal length such that its focal point is midway along the path of the beam between the scanning mirrors 128a and 130a. The dashed lines in FIG. 20A illustrate that the entrance pupil 202 of the objective lens 138 is imaged between the scanning mirrors. Accordingly the beam will walk across the entrance pupil 202 as it scans due to the deflection of both scanning mirrors 128a and 130a, but only half as much from either mirror as would be the case if the first telescope lens 132 focal length was shorter or longer and focused only on one of the mirrors 128a and 130a. Since the walk of the beam is less in both orthogonal directions, the telescope can readily be designed with sufficient magnification to cover the entire entrance pupil 202.

Returning to FIGS. 16, 17 and 18 it will be seen that the objective 138 has a stationary barrel 176. The objective lens 138 has a barrel 170 which is engaged as it moves by a tube 168 of flexible elastomeric sealing material which prevents splatter from the specimen from entering the case and contaminating the internals of the microscope. The seal provided by tube 168 is at the end of the nose 169 of the hand piece 102, which nose also contains the objective 138 and its actuating support mechanism. The objective 138 is in front barrel 170 attached to a rear barrel 172. The rear barrel 172 is a sleeve moving axially (in the Z direction) over a stationary support tube 176. The rear barrel 172 has a slot 174. A screw 163, which extends from the support tube 176 into the rear barrel 172, restricts movement of the objective 138 via its barrels 170 and 172 to axial movement over the distance set by the axial length of the slot 174. The rear end of the support tube 176 is attached to the forward end of a chassis 190 on which the optics and other components of the internals of the hand piece are mounted. The movement of the barrels and the objective 138 is effected by a linear actuator 178 which provides a focus control servomotor (see also FIG. 1 at 178). The motor provides for translation along the Z direction 165 (FIG. 17) against a bias of a spring 180. The spring 180 is attached to the front end of the chassis 190 and to collar 167 having a stub 171 engaged and pushed by the actuator 178.

The nosepiece 169 has a collar 164 at the front end thereof which receives the ring 106; called a tissue ring, since it can press against a location on the skin tissue of the patient and also hold the window 108 against the tissue at the selected location. The tissue ring 106 may have magnetic material which is attracted by magnets 166 between the collar 164 and the nose 169 of the case thereby facilitating the attachment and removal of the tissue ring 106 and its window 108. The window may be a glass disc, but other material may be used.

The chassis 190 is connected to the case via by vibration mounts 148 including pads of rubber. The mounts 148 are positioned to provide a soft interconnection between the case and the chassis 190. Mounting screws attach the case to the chassis via holes 118 (FIG. 16) and 192 (FIG. 18). The chassis is also suspended from the top thereof, as viewed in FIG. 16 by the resilient three-point connection provided by vibration isolation pads in the three mounts 148.

The laser 122 has a mounting barrel 150 which is attached to the upper face of the chassis (as viewed in FIG. 18) by an adjustment mount 154 having three plates, namely face, intermediate and end plates 155a, 155b and 155c, respectively. The laser barrel is mounted to the face plate 155a and passes through the plates 155c and 155b. The end plate 155c is connected to the chassis by an L-shaped mount 194. A first flexure strip 154a and a second flexure strip 154b, between the plates 155c and 155b, and 155b and 155a, respectively, enable tilting of the laser in different orthogonal directions. The desired tilt for laser alignment can be obtained by adjustment screws which extend through the mount via holes 157. Accordingly, the mount 154 facilitates angular adjustment of the beam so that it is aligned with the mirror 124.

Figure 16:
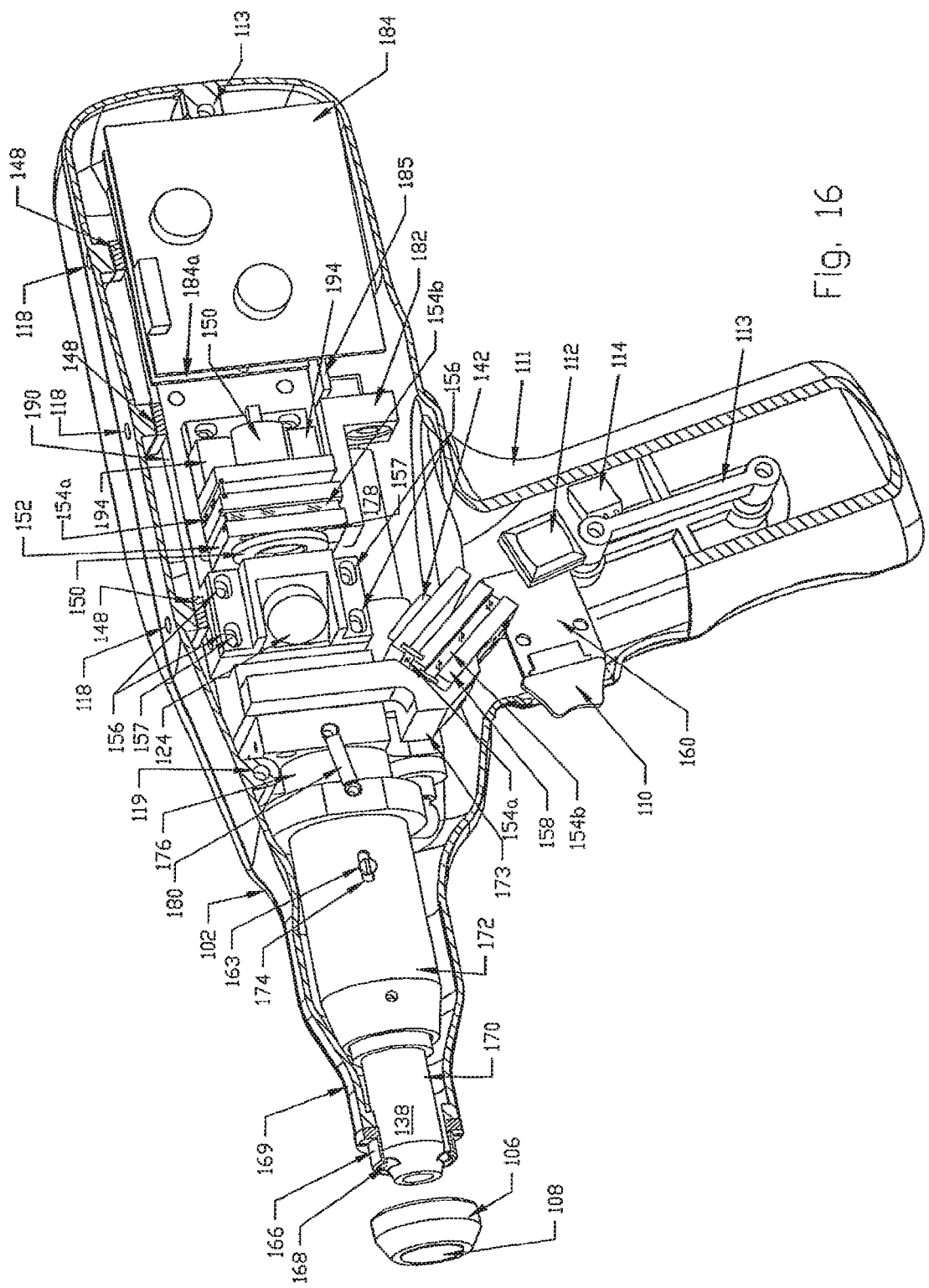
FIG. 16 is a perspective view of the hand piece in the same position as shown in FIG. 12, the cover containing the internals of the hand piece, which are shown schematically in FIG. 15 are exposed, such internals shown in FIG. 16 being rotated 90° clockwise, as viewed from the front in FIG. 15.
Figure 17:
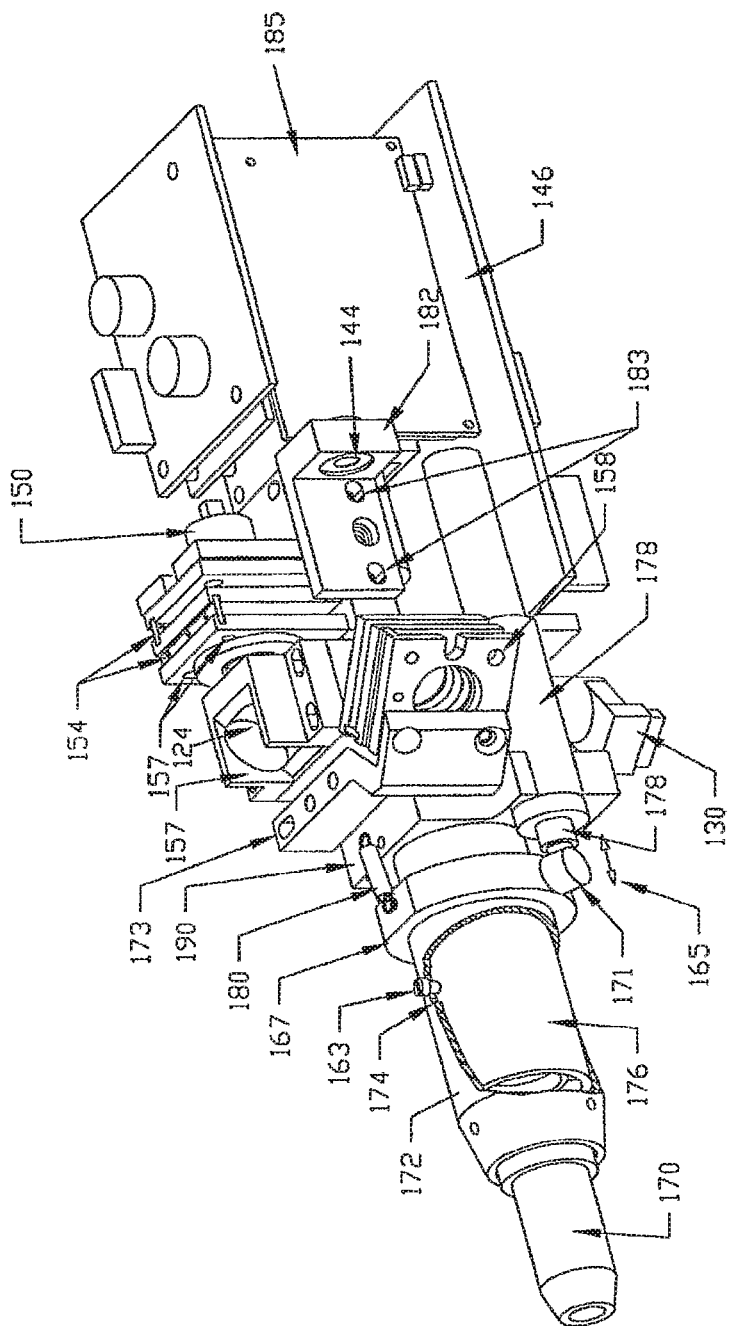
FIG. 17 is a perspective view of the internals of the hand piece which are shown in FIG. 16 with the cover encasing the internals removed and the handle of the hand piece removed. The view being rotated 90° in the counter clockwise direction from the front (the left end) as shown in FIG. 16.

The mirror, as shown in FIG. 16, is attached to the same surface of the chassis 190 as the laser 122 by adjustment screws 156 which pass through slots in a mirror mount 157. The mirror 124 is therefore adjustable toward and away from the laser 122 so as to align the laser with the scanning mirrors 128a and 130a, which are contained in a housing 175 (FIG. 18), also attached to the chassis 190, or which is an integral part of the chassis 190.

The mirror 142, which bends the return light from the beamsplitter 126 via the focusing lens 140 and directs that light to the photodetector 144, is mounted on a tilting mount 158 similar to the mount 154. The mount 158 has its rear plate attached to the chassis via a bracket 173. The photodetector 144 is also connected to the chassis 190 by an L-shaped bracket 182 which is movable along slots 183.

Figure 18:
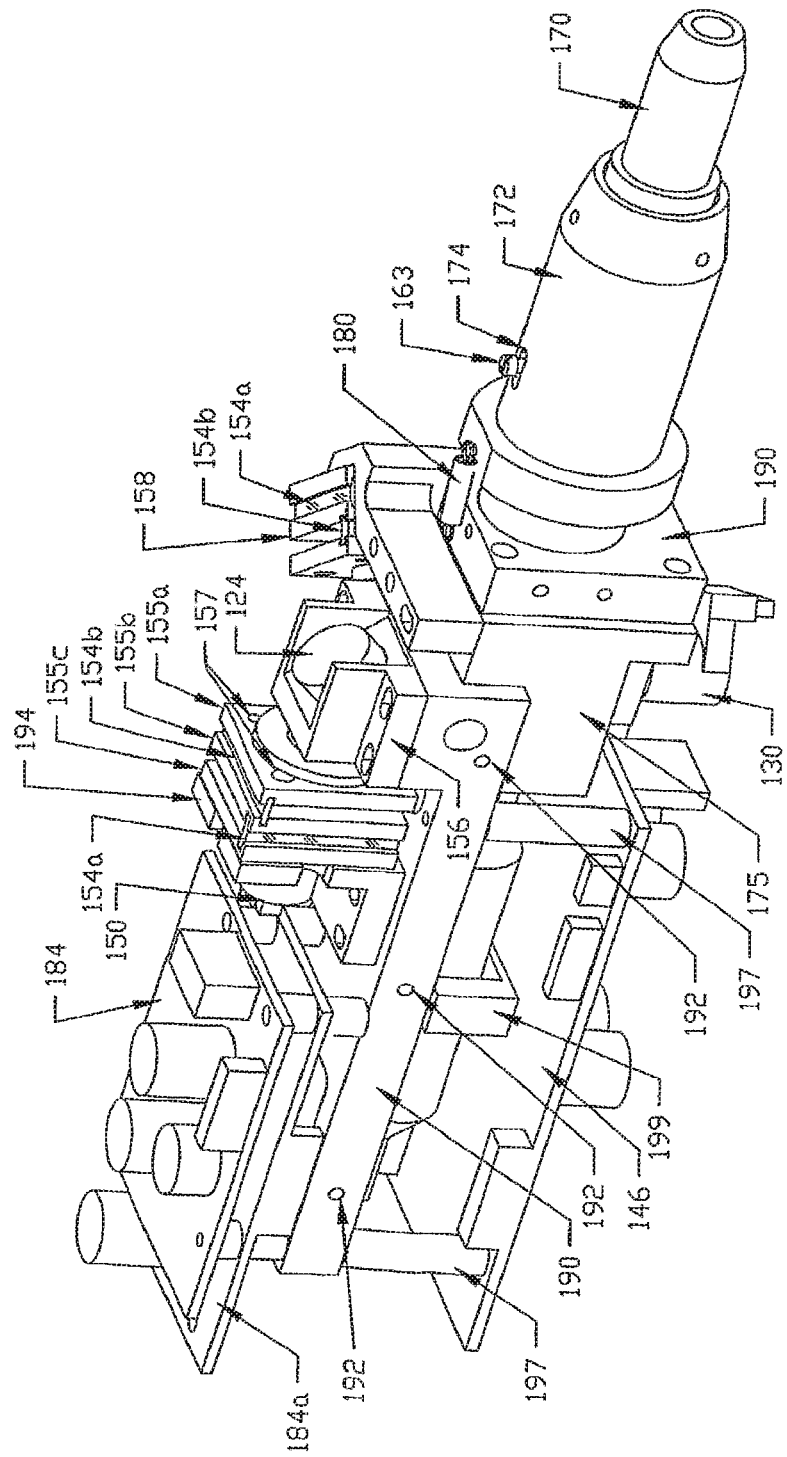
FIG. 18 is another perspective view of the internals of the hand piece with the handle removed; the view being similar to FIG. 16 but taken from the opposite side from the view shown in FIG. 17.

The resonant scanner 128 is anchored to the chassis 190 by means of a yoke 199, and the control board 146 is mounted to the chassis via standoffs 197, as best shown n FIG. 18. The motor of the galvanometer 130 may be connected directly to the chassis 190. Similarly, the linear actuator 178 (FIG. 17) for reciprocating the objective barrel tube 172, which slides over the support tube 176 may be attached to the chassis 190. Accordingly, the internals of the confocal microscope are integrated into a compact package which facilitates hand held operation.

Referring more particularly to FIG. 1, there is shown the electronics of the confocal laser scanning microscope for the configuration and optics discussed above. The electronics are primarily responsible for controlling a solid-state laser diode 122 and the electromechanical devices which produce the illuminating laser raster, namely, resonant scanner 128 and galvanometer scanner 130 which are responsible for the fast- and slow-scanned axes, respectively. The galvanometer 130 may suitably be a commercially available device. The galvanometer available from Cambridge Technology, Inc., 109 Smith Place, Cambridge, Massachusetts, 02138 USA, is suitable. Video timing generator 23, using PCLK and start of scan (SOS), counts scanned pixels and lines and is responsible for generating the usual video synchronization signals which provide horizontal and vertical sync (HSYNC and VSYNC). Timing generator 23, driven via the parallel data bus interface 17 using values programmed by microprocessor 18, generates the active (image scanning) and vertical retrace intervals (and hence the vertical retrace signal in LINE output to the galvanometer 130).

Figure 14:
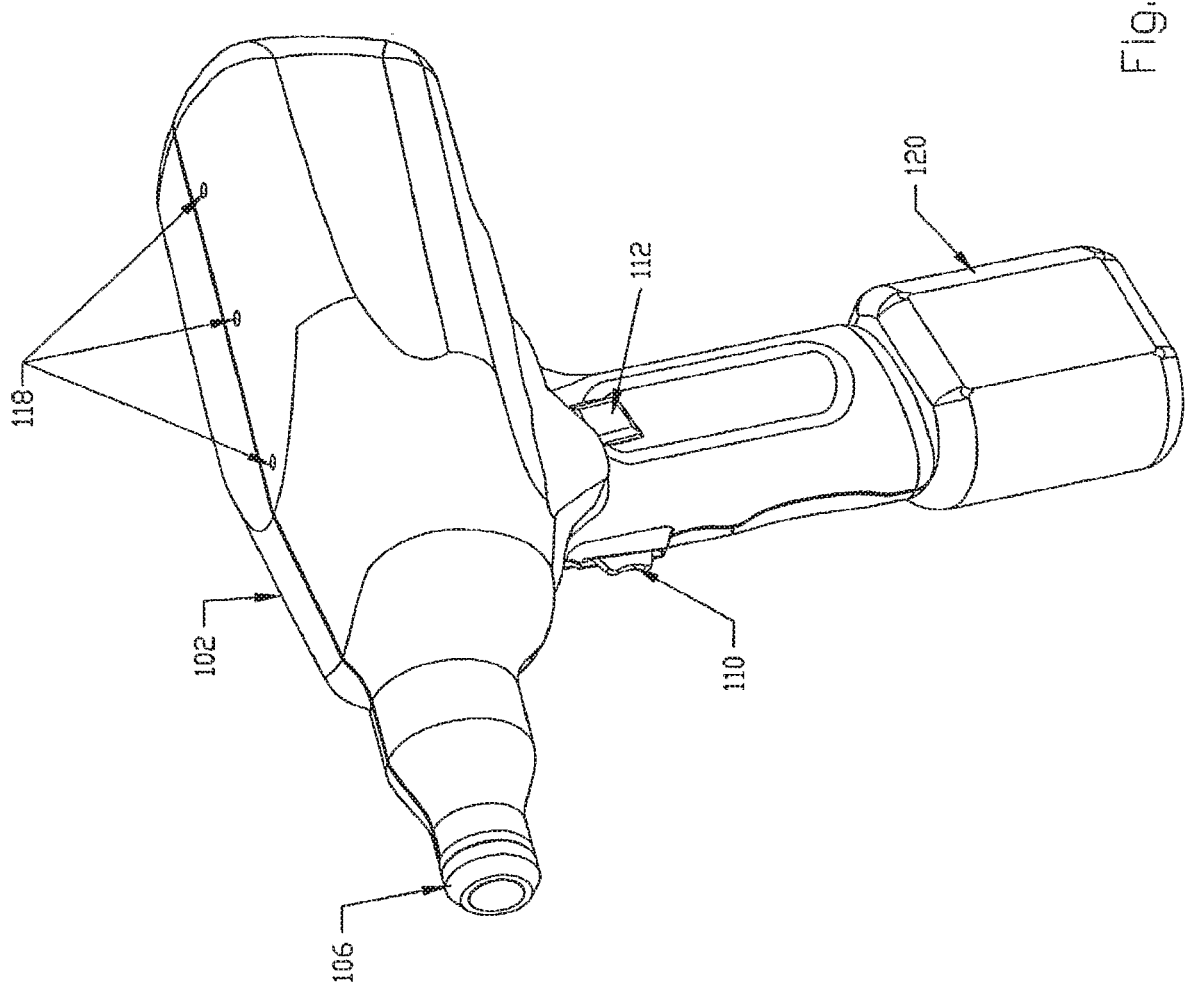
FIG. 14 is a perspective view of the hand piece similar to FIG. 13 but utilizing a battery pack attached at the lower end of the handle of the hand piece.

Light refracted (returned) from the raster scanned laser spot is collected by the optics of the confocal microscope described above and focused onto photodetector 144 where it is converted to a time-varying current, and ultimately a voltage by transimpedance amplifier 2. The confocal optics reject off-plane refracted light incident on the photodetector 144, thus only the in-focus plane is imaged. Typical conversion sensitivities are on the order of 2 V/microwatt of optical power. The time-varying voltage from transimpedance stage 2 is converted into a digital data stream (digitized video signals) by analog to digital converter 3. PCLK, the non-linear sampling clock, is a sinusoidally modulated (in time of occurrence) clock that is derived from the scanning beam's horizontal (X) position, by the digitized video data along with PCLK. The above mentioned synchronization signals and communication data are presented to serialization logic 22 for encoding and subsequent transport to deserialization logic 27. The deserializer logic may be contained in the PC 109 (shown at 31 in FIG. 1), which drives the display producing the image of the tissue section. Thus, return illumination from the specimen is transmitted for detection by photodetector 144 to provide video signals representing image(s) of a tissue section for use by PC 109. The circuitry up to the PC is in the hand piece of the confocal microscope described above. This circuitry is connected via a flexible cable 104 (FIG. 12) between the hand piece 102 and the PC 31. The inclusion of serializer 22 and deserializer 27 reduce the bulk of wires in the cable connecting the hand piece to the PC, thus reducing the size, weight and stiffness of the connecting cable. Although not essential to the operation of the hand held system, their inclusion makes the microscope more user-friendly. In addition, the cable may carry operating electric power to the circuits and devices in the hand piece. Alternatively a battery pack and wireless link (not shown in FIG. 1) which is attached to the hand piece may be used, as shown in FIG. 14.

Deserialization logic 27 separates the encoded signals back into their encoded components for presentation to the PC. The digital video stream is presented to digital to analog converter 29 which converts the digital stream back into the equivalent analog luminance signal that was originally present at the output of transimpedance amplifier 2. The analog luminance signal amplitude is adjusted by DAC 29 to ensure proper scaling for the video capture board 28, and to delay the signal in time. Synchronization signals are also presented to the video board 28 to identify scanned pixels, lines and frames. Communication data is separated from the video stream and presented to the PC's serial port 30. A low-speed communication link (not shown) between a serial port 30 in PC 31 and microprocessor 18 may be included. Communication data from microprocessor 18 to PC serial port 30 is transported along with high-speed video data through the aforementioned link.

The digital line number (LINE) maintained by video timing generator 23 is used as the basis for the slow scan axis. LINE is presented to digital to analog (DAC) converter 24. Amplifier 37 under the control of digital potentiometer 38 (whose setting is controlled by microprocessor 18) establish the amplitude of the resulting sawtooth signal. The galvanometer controller 25 accepts this signal as its position command for galvanometer 130. Thus, as each line is scanned in the fast axis, an SOS pulse is generated, causing the line counter in video timing generator 23 to increment, causing the input position command to galvanometer controller 25 to slightly increase, in turn causing galvanometer 130 to deflect to a slightly different Y position for each consecutively scanned line, thus forming a raster scanned laser path on the tissue specimen.

Microprocessor 18 performs all system control functions as directed by its operating firmware. This firmware directs it to accept commands from the PC's serial port 30, respond to those commands by carrying out the specified actions, and relay status information via the high-speed serial link formed by serializer 22 and deserializer 27.

DAC 19 provides a voltage to laser driver 20 to establish for laser 122 either laser operating current or laser operating power, depending upon the configuration (of the laser driver). Currently, a current regulating lasers is preferred. The laser 122 and driver 20 may be commercially available components. The laser preferably operates at a near infrared wave length to facilitate penetration of the laser beam into the tissue being sampled. However, other wave lengths may be used for two-photon or fluorescence imaging. As a safety precaution an interlock switching circuit in the driver 20 (not shown) may be responsive to actuation of the pressure sensitive switch 114 (FIG. 13) which is activated when the handle of the hand held unit 104 is grasped to enable operation of the driver only while imaging operations are in progress. The laser 122 may include a photo detector optically coupled to the laser diode to provide a signal to the driver 20 for maintaining the laser power essentially constant.

Microprocessor 18 also controls servomotor controller 32 and its associated servomotor 32a which translates the objective lens for focusing the microscope to image a desired section on or in the tissue or other specimen. Together these components control the microscope's imaging (focal) depth. Commands are generated by the toggle switch 110 (FIG. 12) and sent from an application program running on the PC, via cable 104, logic 22 and interface 17 to microprocessor 18's firmware control the motor's position.

The remainder of circuitry controls the operation of resonant scanner 128 and the generation of VCO clock. VCO clock is an integer multiple of the video data sampling clock PCLK. The division is performed by serialization logic 22.

Referring again to FIG. 1, the resonant scanner control system is shown to involve microprocessor 18, resonant scanner drive 5, power driver 6, resonant scanner 128, amplifier 8, low-pass filter 9, programmable gain amplifier 10, digital pot 11, summer 13, peak detector 35, ADC 36, comparator 15, and phase measurement 16. ADC 36 is preferably part of microprocessor 18 and is carried out the frequency and angle control programs described in FIG. 8-FIG. 11. Resonant scanner control is logically divided into two aspects: frequency and amplitude control. These parameters are controlled by a dual-variable control loop implemented with the control programming presented below.

Microprocessor 18 generates pulses of controlled frequency and duration using resonant scanner drive circuit 5. These pulses are power amplified by power driver 6 and applied to the drive coil of resonant scanner 128. As a result of the drive pulses, the scanner oscillates producing a measurable velocity signal at the output of amplifier 8. This signal is converted to a digital absolute value by comparing it to zero volts. A high logic level is produced by comparator 15 when the scanner's velocity is positive, and a logic low is produced when the scanner's velocity is negative. This signal is routed to phase measurement circuit 16 which measures the scanner's relative phase by counting the number of clock cycles from the turn-off edge of drive pulse A (DRIVEA) to the falling edge of the SOS signal in terms of the number of reference clock 39 cycles which elapse between the two events. This numerical value is taken to be the measured phase, and is presented to microprocessor 18 via parallel data bus interface 17. At preset intervals, preferably every 320 milliseconds, microprocessor 18 retrieves measure phase values, uses them in the PID Calculation program (FIGS. 10 and 11), and changes resonant scanner drive 5 FREQ input as a result of the calculation. In doing so, a closed frequency control loop is formed which maintains a constant measured phase value, which represents a 90° phase shift between the resonant scanner's drive waveform and its mechanical motion, thus insuring the scanner operates at its natural frequency.

A secondary scan angle control loop is formed by monitoring the amplitude of the ANGLE signal at the output of peak detector 35 using ADC 36 and adjusting the duty-cycle of the drive pulse waveform applied to resonant scanner 128 drive coil. Samples of the ANGLE signal are taken every 10 milliseconds. 32 such samples are summed to reduce the effect of noise, resulting in a numerical value that is 32 times the numerical average. While a division might be performed that computes the numerical average (e.g., dividing the sum by 32), it saves processing time for the desired reference value to be multiplied by 32 once at the on-set of scanning to obtain the desired numerical value for direct comparison to this summed value. The resulting numerical value of the 32 summed values is compared to 32 times the reference value, and the signed difference, scaled by a numerical constant, is used to adjust the scanner's drive pulse on-time established by TON. Because resonant scanner 128's drive frequency is confined to a rather narrow operating range, a few hundred hertz around its nominal room temperature operating frequency of 7,950 Hz, TON (which directly controls drive pulse on-time), controls duty-cycle, and hence average power applied to the scanner's drive coil, and therefore scan angle for any given drive frequency. Also, TON can be selected to provide the scan angle corresponding to a desired image zoom (magnification).

As with frequency adjustment, TON is adjusted every 320 ms. The frequency control loop so that makes small frequency adjustments (e.g., the frequency control loop is locked onto the correct resonant frequency. Thus the dual-variable digital control loop is formed that acts to maintain 90° phase relationship between the scanner's motion and drive waveforms, and acts to maintain a constant amplitude scan angle oscillation.

The dynamic control of scan angle (electronic zoom) is implemented in the sample clock spatial linearization circuits 10,11, and 13 and if both forward and reverse scans are used for successive lines of the raster, in addition with absolute value circuit 12 as discussed below in connection with FIG. 6.

Figure 2:
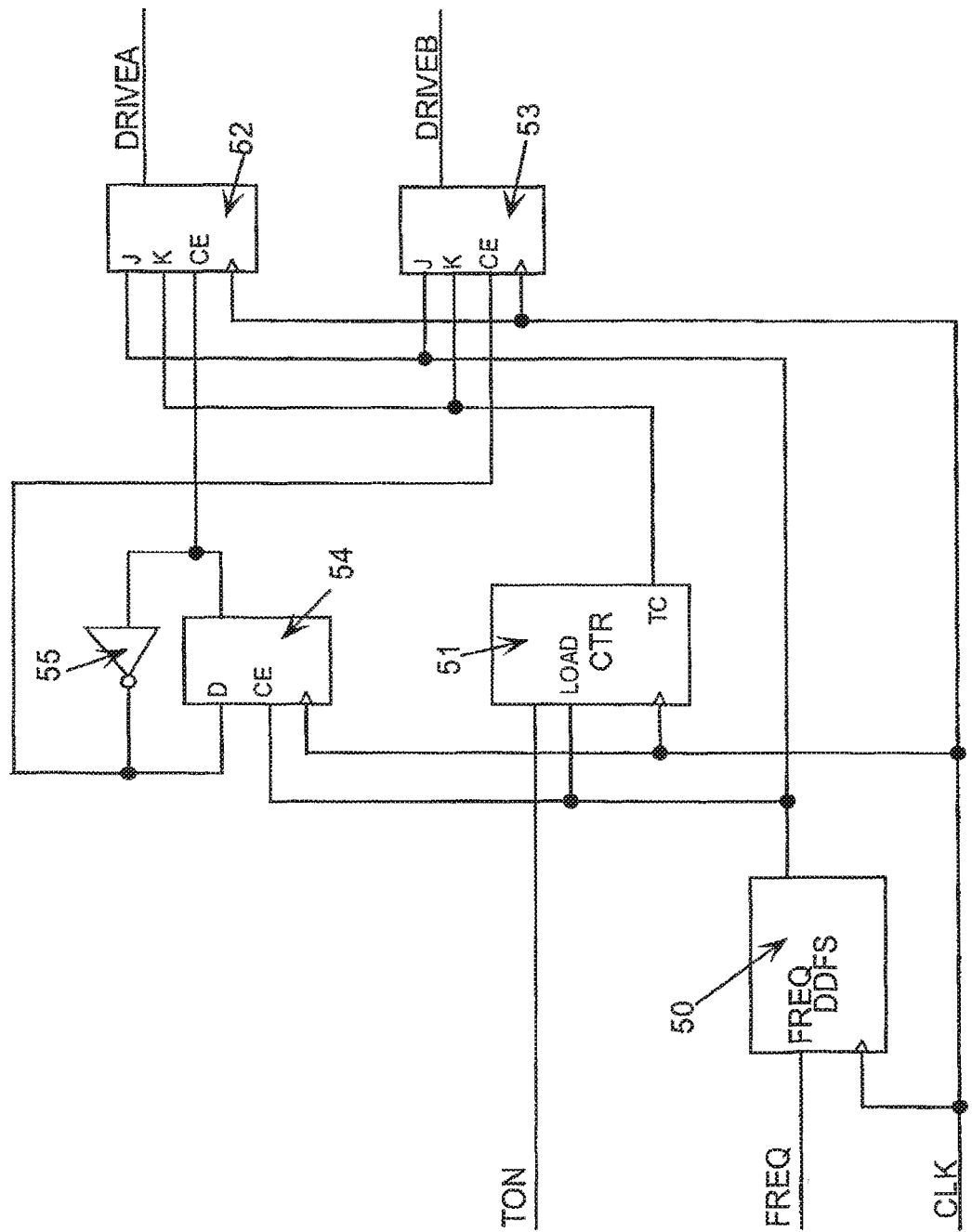
FIG. 2 is a block diagram which shows the drive circuits of the resonant scanner of FIG. 1 in detail; the drive circuit being labeled resonant scanner drive in FIG. 1.

FIG. 2 shows the digital control circuit used to generate precisely controlled width and frequency pulses which are subsequently power amplified by power driver 6 and applied to the drive coil of resonant scanner 128. The FREQ input precisely controls drive pulse frequency, and the TON input precisely controls drive pulse on-time. Frequency control uses DDFS 50 which is detailed in FIG. 3. DDFS circuit operation is discussed in detail in the public domain article, Austin Lesea, FPGA Applications Frequency Synthesis, Xcell 31, pp. 32-33, 1999, available at Xilinx, Inc. website at xilinx.com.

The DDFS method of output frequency control is preferred for resonant scanner control because it provides precise frequency control. The derivative with respect to FREQ, the input value, gives the frequency change per count as $$\frac{Fclk}{2^k},$$

where k is the number of bits in DDFS circuit. In effect, k can be made as large as needed to produce sufficiently precise frequency control. For the preferred implementation k is 32 and with an 80 MHz reference oscillator 39, precise frequency control to better than 20 mHz (millihertz) is possible.

From equations given in the reference article by Lesea, the output frequency of DDFS 50 is equal to:

$$f_{DDFS} = f_{reference\_clock} \cdot \frac{(845,572 + FREQ)}{2^{32}} \qquad (2)$$

Simplifying equation (2) and substituting the circuit values gives:

$$f_{DDFS} = (15,750.006 + 0.01826 \cdot FREQ) \text{ Hz} \qquad (3)$$

The fixed frequency value in equation (3) represents twice the resonant scanner's lower-frequency (per manufacturer's specification) plus 15% of that lower frequency. Negative values of FREQ reduce drive frequency, positive values increase it. As will be discussed, this biased frequency output insures that the "hunting" term in the DDFS program (FIG. 9) will converge on a frequency solution during start-up when the scanner's motion may be too small to measure.

Each output pulse of DDFS 50 alternately triggers JK flip-flop 52 or 53 which generate DRIVEA and DRIVEB output pulses, respectively. D flip-flop 54 and inverter 55 together form a toggle flip-flop that alternately select output flip-flop 52 or 53 to receive the pulse. Simultaneously, counter 51 is preset to the value of TON, which represents the drive pulse duration in terms of reference clock 39 cycles. Once counter 51 down-counts to zero, its TC output activates clearing the active DRIVEA 52 or DRIVEB 53 flip-flop via their "K" input.

Figure 3:
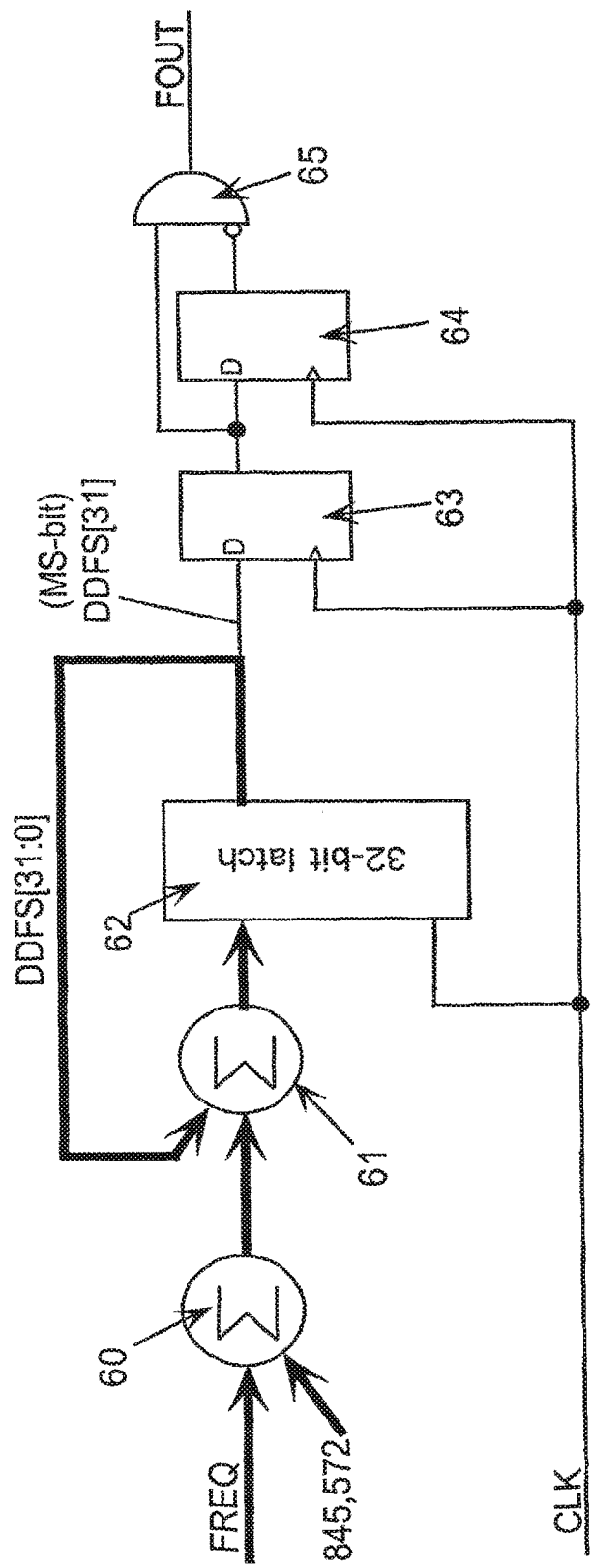
FIG. 3 is a block diagram which shows the DDFS (direct digital frequency synthesizer) of the resonant scanner drive shown in FIG. 2 as FREQ DDFS 50.

FIG. 3 implements the DDFS circuit. 32-bit latch 62 is loaded with a numerical value that is (FREQ+845,572) larger than its current value on each consecutive rising reference clock edge. In doing so, the most-significant bit changes with a frequency given by equation (3). Flip-flops 63, 64 and AND gate 65 form digital logic providing an edge detector. This circuit produces one single output pulse on the rising edge of its input. Note that if the (inverted input) is moved to the other side of the AND gate, the circuit detects falling-edges. In doing so, a pulse stream of the indicated frequency whose durations are exactly one reference clock cycle wide are produced.

Figure 7:
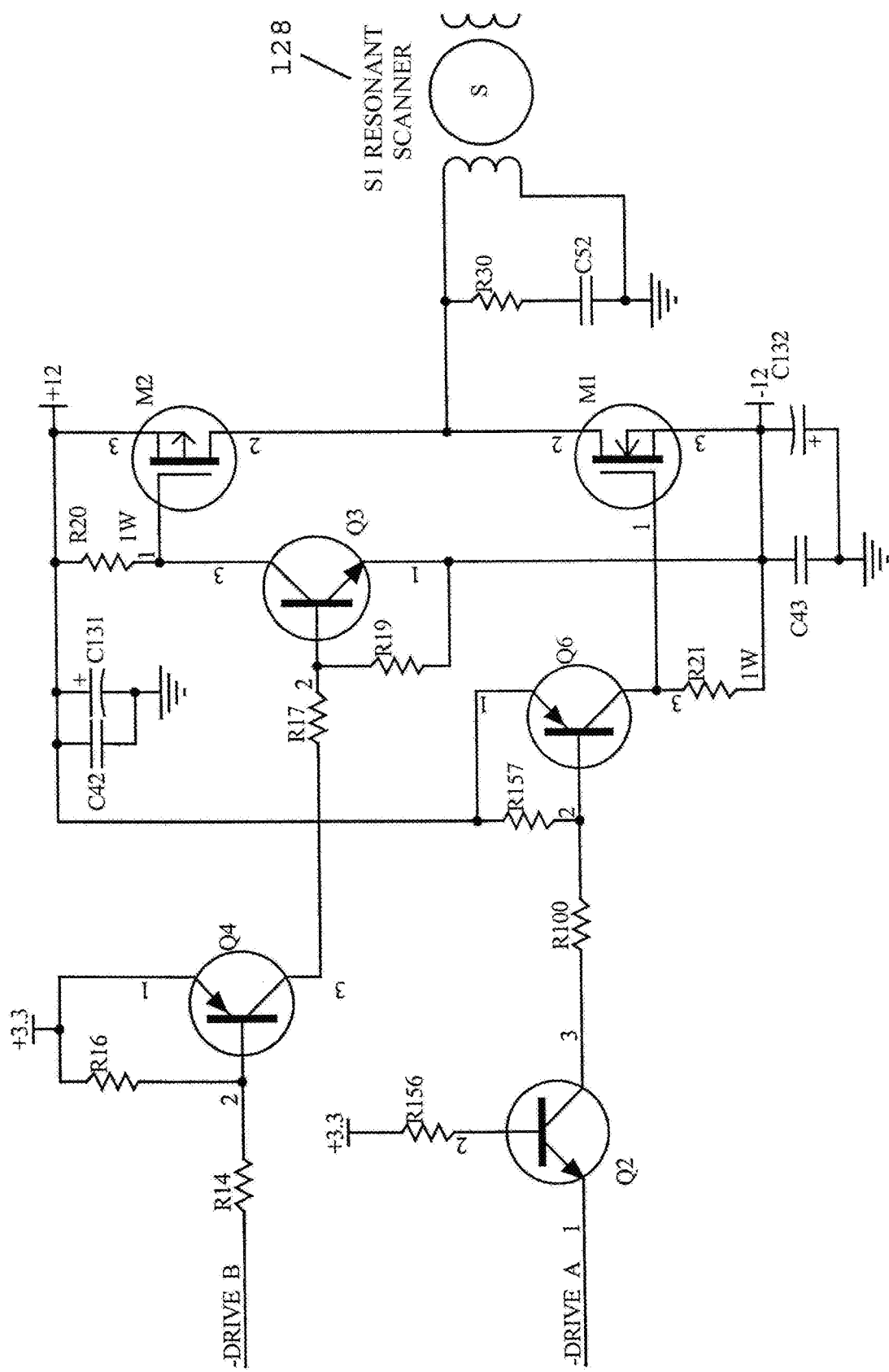
FIG. 7 is a schematic diagram of circuits which deliver drive pulses to the drive coil of the resonant scanner, the circuits being labeled the power driver 6 in FIG. 1.

FIG. 7 shows power driver 6 (from FIG. 1) in detail. Resonant scanner 128 drive coil is alternately pulsed in the positive current direction by saturated MOSFET switch (M2), then in the negative current direction by saturated MOSFET switch M1. Note current direction assignment is arbitrary and selected only for purposes of this description. Flyback diodes fabricated within MOSFETs M1 and M2 suppress dI/dt induced switching transients caused by the rapid turn off of M1 and M2. An additional R-C snubber circuit formed by R30 in series with C52 is included to further suppress inductive switching noise. Voltage level translation stage formed by Q4, R14 and R16 translate the logic level of the −DRIVEB signal from the FPGA logic system to the levels required by M2's gate. Inverter Q3 along with its associated biasing resistors R17, and R19 provide a signal inversion and further voltage level translation. Logic levels of the −DRIVEA and −DRIVEB (28) are chosen to be active low to insure MOSFETs M1 and Ms are off during FPGA programming and initialization (e.g., before the FPGA's logic functionality is defined). Similarly, voltage level translation stage Q2, R156, R100, R157 and Q6 perform a level translation and inversion between the FPGA output −DRIVEA and the levels required by the gate of MOSFET M1. A feature of the herein described circuit is that the scanner moves symmetrically about its rest position because it is pulsed in both the forward and reverse directions in each oscillation cycle.

Figure 5:
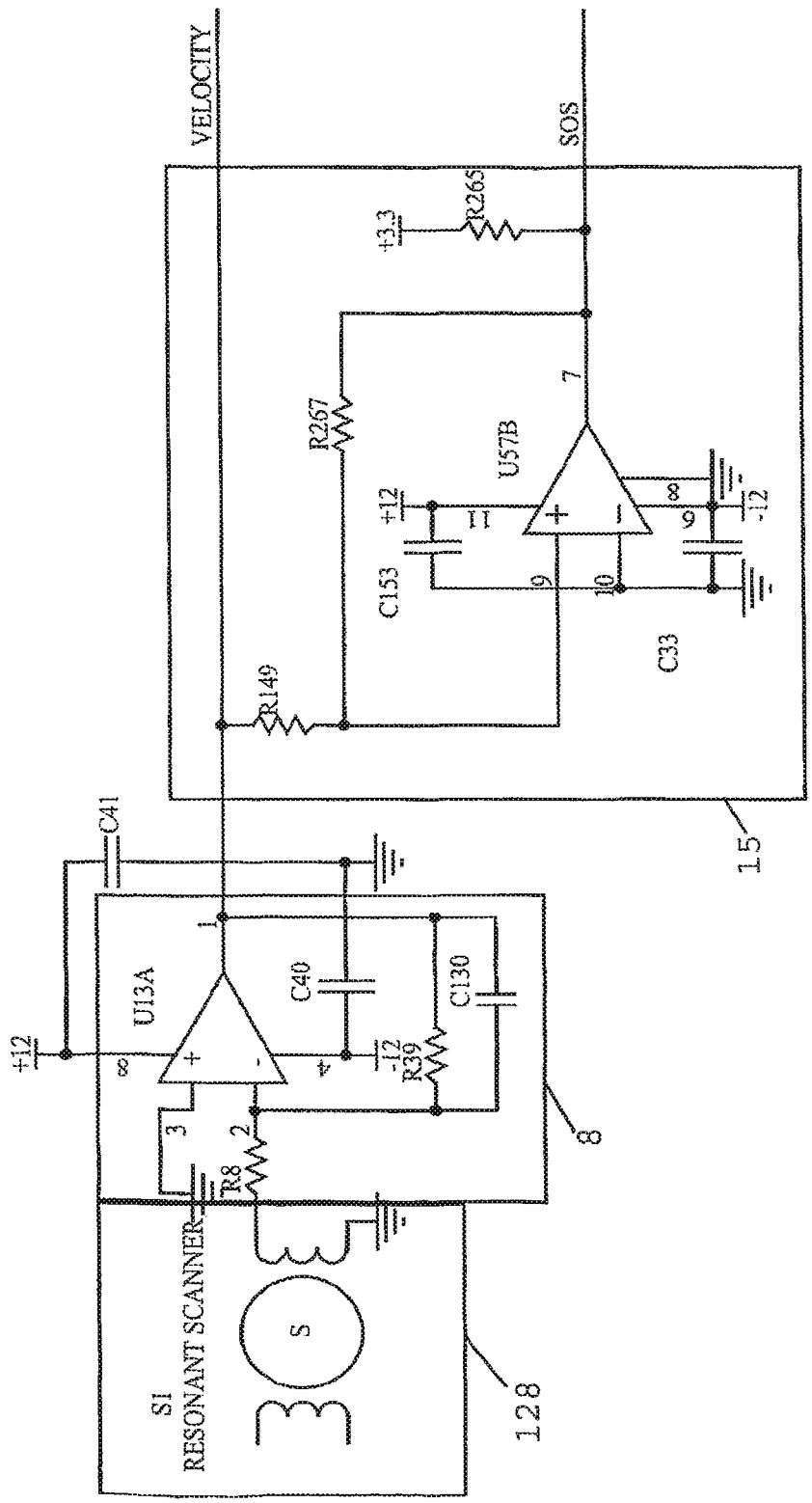
FIG. 5 is a schematic diagram which shows the velocity signal conditioning circuits (items 8 and 15 of FIG. 1) in detail; these circuits providing the start of scan (SOS) signal.

FIG. 5 shows the scanner's sense coil conditioning circuitry. The sense coil of scanner 128, since it is in the presence of a moving magnet (attached to the torsional element), induces a signal proportional to the mirror (128a FIGS. 12-20) velocity. Because the mirror's velocity is sinusoidal by virtue of resonant scanner 29 high-Q, the amplitude of the velocity term is also proportional to total scanned angle. This signal is amplified by the band-limited, inverting amplifier stage formed by op-amp U13A, resistor R39, and capacitor C130. The gain on inverting amplifier stage 13 is sufficiently large so driving the resonant scanner flexure well off its resonant frequency produces a detectable output. Typically this gain is −10.

The output signal, named VELOCITY, is fed into comparator U57B with hysteresis resistors R148, R267 and R265. The resulting digital signal, SOS 18 (start of scan), is used to measure the scanner's phase as already described herein. A delayed-in-time copy of this signal provides the horizontal synchronization pulse required by the video capture board 28 (FIG. 1). By making the time-delay variable, the video image can be electronically shifted on the display in the horizontal direction to compensate for optomechanical alignment variation.

Figure 4:
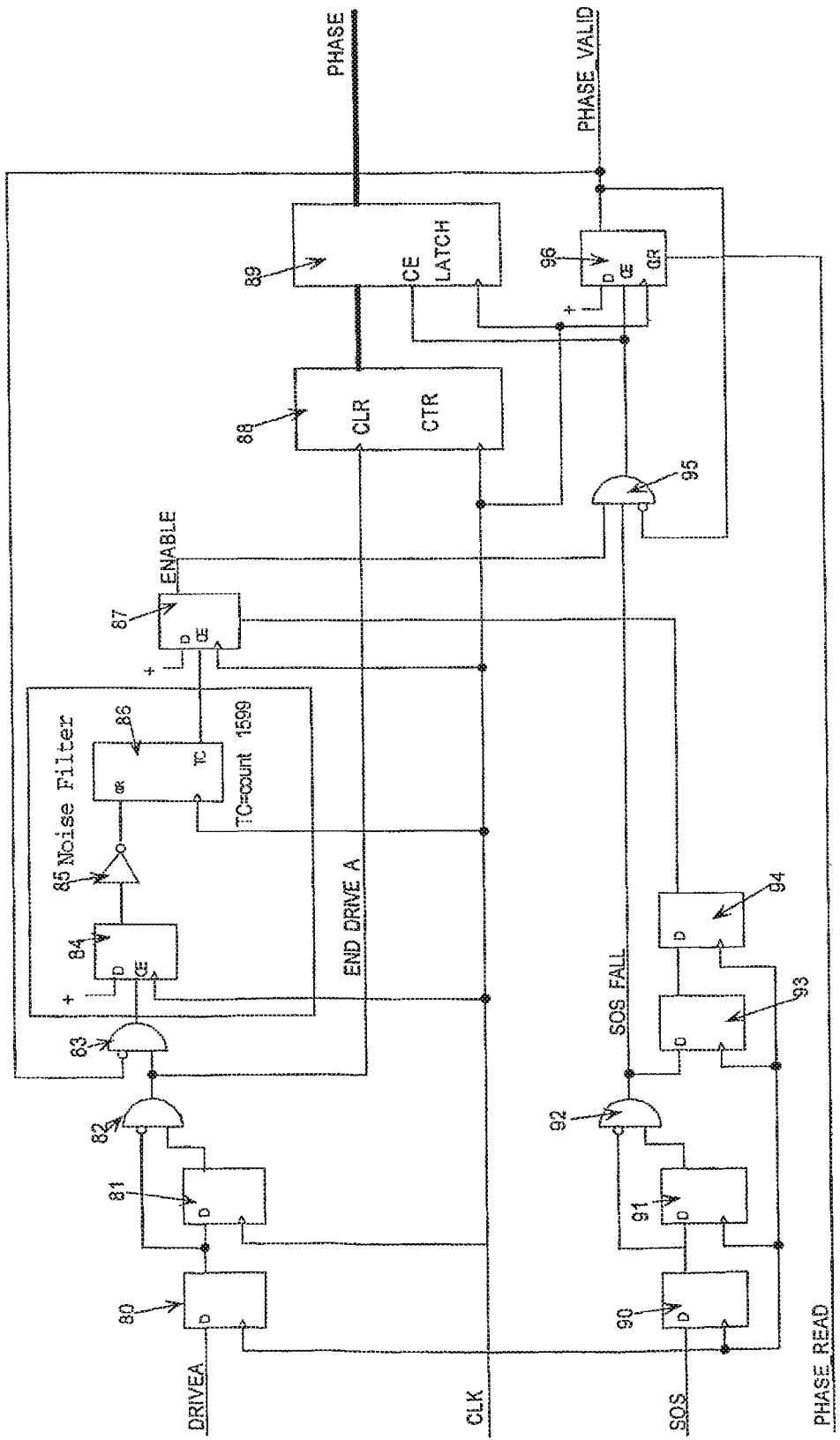
FIG. 4 is a schematic diagram which shows the phase measurement circuit of FIG. 1 in detail; the phase measurement circuit being indicated in FIG. 1 at reference numeral 16.

FIG. 4 shows phase measurement circuit 16 (FIG. 1) in detail. The process begins with the end (falling edge) of DRIVEA, as detected by the edge detection circuit formed by flip-flops 80, 81 and AND gate 82. This pulse sets flip-flop (FF) 84 via AND gate 83. FF 84 setting enables the noise filter that inhibits measurement for the following 20 μs. The noise filter prevents the circuit from detecting noise pulses on the SOS signal that result from d/dt transients following the scanner drive coil turn-off. Counter 86 enabled by the setting of FF 84, counts up 1600 reference clock pulses generating the 20 μs delay (1600/80 MHz=20 μs). Upon terminal count, enable FF 87 sets, enabling the latching of a valid phase measurement. Timing counter 88 is cleared at the end of DRIVEA, and proceeds to up-count reference clock cycles until the falling edge of SOS is detected by the edge detection circuit formed by FFs 90, 91 and AND gate 92. This pulse passes through AND gate 95, causing latch 89 to latch the measured phase value present at the output of counter 88, and setting the phase valid FF 96. Microprocessor 18, by virtue of parallel data bus interface 17 periodically polls this bit to determine if a phase measurement is available. The SOS FALL pulse is delayed two clock cycles by FFs 93 & 94 then clears the ENABLE FF 87. Further phase measurements are inhibited by AND gates 93 & 95 while PHASE_VALID FF 96 remains set. When microprocessor reads the latch phase value, a pulse is generated on the PHASE_READ signal clearing the PHASE_VALID signal, enabling the next measurement cycle.

Accordingly, the resonant scanner is driven with a bipolar pulse waveform whose frequency and duration are controllable by microprocessor 18. Further, microprocessor, by virtue of phase measurement circuit 16, measures the scanner's movement relative to the drive waveform. And finally, peak detector 35 and ADC 36 allow microprocessor 18 to monitor the scanner's resulting scan angle. Together, these circuits facilitate the closed-loop digital control system for driving resonant scanner 128 at its resonant frequency and controlling its total scanned angle.

The VELOCITY signal derived during discussion of FIG. 5, is further conditioned to generate a frequency modulated clock that serves as the basis for video sampling and pixel identification. FIG. 6 shows the sample clock, (spatial) linearization circuitry (items 9-11, 13, 14, 34 & 35 of FIG. 1 in detail).

As mentioned earlier, the scanner's position, (actually its negative), is derived from the VELOCITY signal using a low-pass filter rather than an integrator. R152, R153, C122-124 form a two-pole low-pass filter. The filter's output is routed to the band-limited variable gain amplifier formed by op-amp U28A, R96, C125 and digital potentiometer U18. Microprocessor 18 controls the resistance of U18 and thus the overall gain of amplifier U28A. Amplifier U28D, along with its biasing network R98, R99, and C126 comprise summer 13 (FIG. 1). The purpose of this summer is to level-shift the POSITION signal (at the output of U28A) to insure it remains within the dynamic input range of VCO 14 (FIG. 1). DC analysis of amplifier U28D and its associated bias network provides the output voltage of summer 13 in equation (4):

$$V_o = \left(1 + \frac{R_{99}}{R_{98}}\right) \cdot \text{POSITION} - \left(\frac{R_{99}}{R_{98}}\right) \cdot (-1) \tag{4}$$

POSITION in Equation (4) is the voltage at the output of amplifier U28A.

Voltage reference U29 and biasing resistor R97, together with inverting amplifier U28B and its bias network R61 R155, C39 form a −1.0V reference voltage. This voltage is algebraically subtracted from the POSITION signal by U28D as shown in equation (4). The resulting voltage is the input to VCO U25 (which is the implementation of item 14 on FIG. 1).

Finally, bias network R154, R62 R38, R143, comparator U59A, transistor Q34, R268, C108 implement peak detector 35 of FIG. 1. Follower amplifier U28C buffers the high-impedance node at C108 to prevent loading by ADC 36. When the voltage at U59A pin 5 exceeds the voltage across C108, comparator U59A's output switches low, turning on Q34 through R38. Q34's collector current charges C108 until its voltage equals U59A pin 5, at which time the comparator's output switches high, turning off Q34, stopping additional collector current. Because there is essentially no current load on C108 (except R268), C108 remains charged to the peak voltage on pin 5. R268 is provided to slowly discharge C108 in the event that transients cause it to become overcharged during power stabilization. Therefore, the voltage across C108 and at the output of buffer amplifier U28C is the peak voltage at the VCO input scaled by the voltage divider formed by R62 and R154.

U25, may be the VCO portion of a phase-locked-loop chip manufactured by Texas Instruments as TLC2932 or TLC2933, and implements of VCO 14 in FIG. 1. Digital pot U24 implements item 34 (FIG. 1) and sets the base VCO operating frequency under control of microprocessor 18. U24's output frequency varies linearly as the VCO_IN signal varies from 1 to five volts, thus producing the sinusoidally modulated VCO Clock signal discussed above.

As mentioned earlier, it may be desirable to collect video data during both the forward and reverse scanning directions of resonant scanner mirror (128a, FIGS. 19, 20A and B), effectively doubling the frame rate (e.g., because line rate is fixed by the resonant scanner's resonant frequency, collecting data on both the forward and reverse scan effectively doubles the line rate). The system described above then: 1) the includes absolute value circuit 12 (of FIG. 1) the output of which is now POSITION; 2) the POSITION signal (output of absolute value circuit 12) is applied to comparator 15 is increased; 3) the threshold voltage of comparator 15 is increased to be slightly above ground, nominally 50 to 100 mV; and 4) of video data LIFO buffering memory is included to reverse presentation of data to the video display on alternate scanned lines.

The following description relates to the firmware and programming aspects of the close-loop resonant scanner control provided by the invention. Note that the microprocessor 18 provides the circuitry heretofore discussed in programming the field programmable gate array FPGA 4 (FIG. 1).

From a firmware perspective, scanning is an autonomous process, with exception of brief but periodic numerical calculations. As such, it is generally preferred to trigger the task using a programmable timer in the microprocessor 18 which may be Motorola type 68HC908AB32 microcontroller (preferred presently) which is available from Freescale Semiconductor, formerly Motorola Semiconductor Corporation, 6501 William Cannon Drive West, Austin, Texas 78735. The 68HC908AB32 has two internal times, one of which is dedicated to this programmable timer function.

The firmware not shown in detail herein provides conventionally for device initialization, accepting and interpreting commands from the host PC, responding to those commands by carrying out their associated actions and relaying the outcome of commands to the host.

The control system provides for the initial locking onto the resonant scanner's frequency. When the scanner is first started, it's operating temperature, and hence its exact operating frequency are unknown. Moreover, a frequency error of a few hundred Hertz results in virtually undetectable movement, and hence no velocity output. Nevertheless the control system controls resonant scanner operation even for the initial part of its operation. To this end, biased-hunting takes place. As mentioned earlier, the drive frequency always begins approximately 15% above the scanner's maximum specified resonant frequency. In the absence of a detectable phase measurement, the program (FIG. 9) decreases the drive frequency by a small, but nonzero delta. In doing so, eventually the control system will lock onto the exact drive frequency by a small, but nonzero delta. In doing so, eventually the control system will lock onto the exact operating frequency by slowly approaching it. Once the system gets sufficiently close to the resonant frequency, resonant scanner 128 will react to the drive waveform by producing a measurable phase signal.

Figure 6:
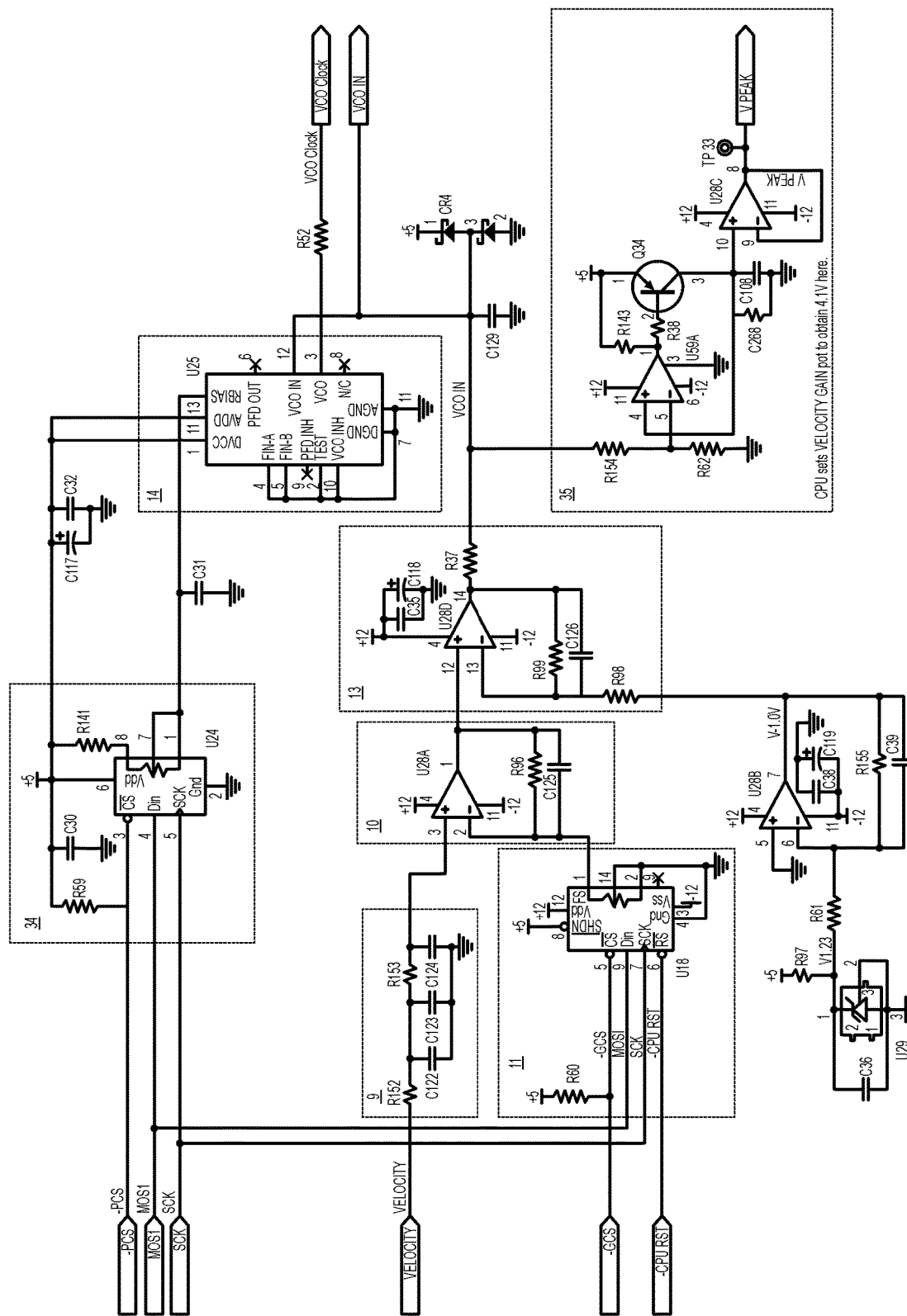
FIG. 6 is a schematic diagram which shows the sample clock linearization circuits and dynamically control magnification to zoom the image (items 9-11, 13-14, 35 and 36 of FIG. 1) in detail.

FIG. 6 shows the spatial linearization circuitry in detail. Also included are the reference numbers from FIG. 1.

Two-pole low-pass filter 9, implemented by R152, R153, C122, C123 and C124 delays the VELOCITY signal to coincide with the exact mirror 128a position. The required delay may be as experimentally determined by monitoring the video luminance and POSITION signals produced by an assembled system. The time delay value may be chosen so that the POSITION signal corresponded with the center of the video frame. The attenuated and delayed signal from low-pass filter 9 is amplified by variable gain amplifier 10, whose gain is controlled by digital potentiometer 11 which is under control of microprocessor 18. The gain of amplifier 10, directly controls scan angle.

Analog adder 13, formed by amplifier U28D, R98, R99 and C126 subtracts the −1 volt supply created by voltage reference U29, and the band-limited inverting amplifier formed by R61, R155 and C39 from the POSITION signal effectively biasing the POSITION signal one volt above ground corresponding with VCO 14's minimum input voltage. Peak detector 35 formed by comparator U59A, bias network R154, R62, and transistor buffer Q34, R143 and R38 detects and maintains the peak of this voltage from scan to scan. Amplifier U28C buffers the high-impedance output of the peak detector from loading effects of subsequent circuitry. This signal, named, ANGLE, is a direct measure of scan angle. ANGLE is converted to a digital value by analog-to-digital converter 36, which is incorporated in microprocessor 18's internal circuitry. Programs discussed in connection with FIG. 9 operate to maintain this voltage at a constant value of approximately 4.5 volts, corresponding to the VCO's upper dynamic input limit by varying resonant scanner 128 drive waveform's on-time by virtue of the value written to TON, the input to pulse width control circuit 51. Peak detector 35's output is maintained at a constant level. Accordingly, by the gain of varying amplifier 10 scan angle is controlled since the amplitude of the unamplified output of low-pass filter 9. Furthermore, microprocessor 18, using digital potentiometer 11 insures the amplified and translated velocity term uses the full input dynamic range of VCO 14. Thus, dynamic zoom corresponding to selected scan angle is controlled via the gain of amplifier 10.

Microprocessor 18 controls base frequency digital potentiometer 34, formed by digital potentiometer U24 and R141 to establish the base frequency of VCO 14, implemented as U25. Base frequency potentiometer 34 controls the number of pixels in each horizontal line.

Therefore, the system produces a pixel sampling clock whose frequency is sinusoidally modulated corresponding to the relative beam position of a laser reflected from resonant scanner 128's mirror. In doing so, the system produces samples that are uniformly spaced across the microscope's field of view (viz., spatial linearization occurs). This clock forms the basis for the pixel sampling clock within serializer logic 22 (see FIG. 1) where it is digitally divided by three, corresponding to the frame packing multiplier.

Further, by maintaining the peak detector output at a constant voltage while varying the gain of amplifier 10, (by varying the resistance of digital potentiometer 11), zooming (dynamically varying) that field of view is obtained, all while driving the resonant scanner's at, or nearly at, its resonant frequency.

Consider next the programs which may be implemented in firmware to implement resonant scanner control with the circuitry described herein.

As mentioned earlier, firmware is periodically invoked via one of the microprocessors internal timer channels. A preferred timer interval may be 10 milliseconds.

Figure 8:
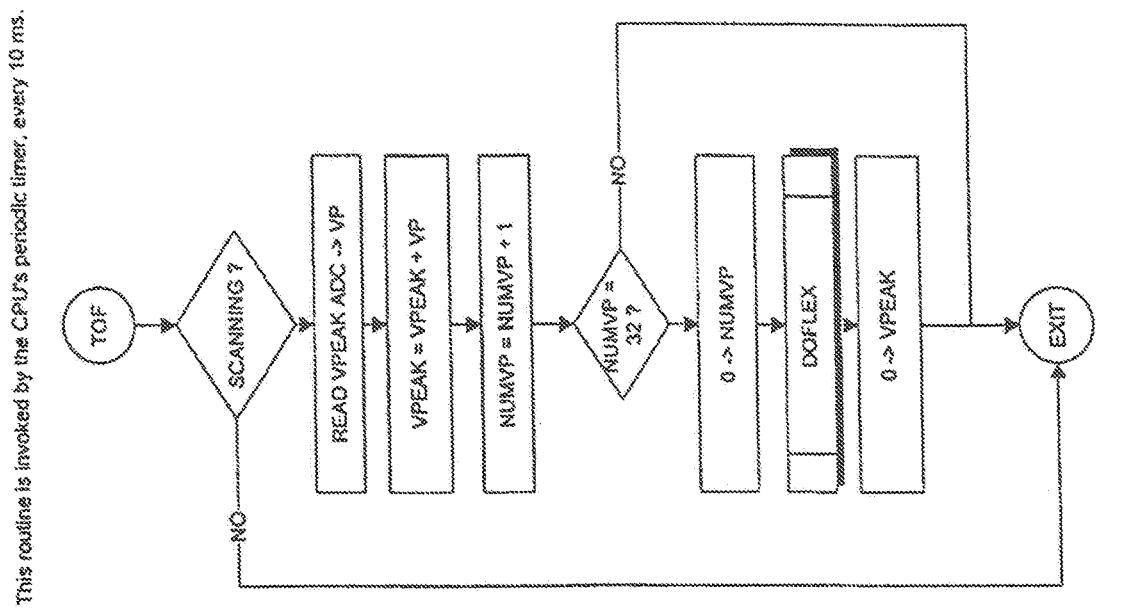
FIG. 8 is a flow chart which shows the program in the microprocessor of the system shown in FIG. 1 which provides the periodic time interrupt.

FIG. 8 shows the TOF (timer overflow) service routine that services the resonant scanner. This routine is invoked every 10 ms. This routine is invoked every 10 ms. The routine determines if the system is scanning (e.g., whether or not resonant scanner 128 in FIG. 1 is operating), and quickly exits when it is not. Assuming scanning is active, the routine proceeds to acquire and sum 32 samples of the ANGLE signal via ADC 36. After 32 samples have been acquired and summed (in the variable named VPEAK), the DOFLEX routine is invoked.

Figure 9:
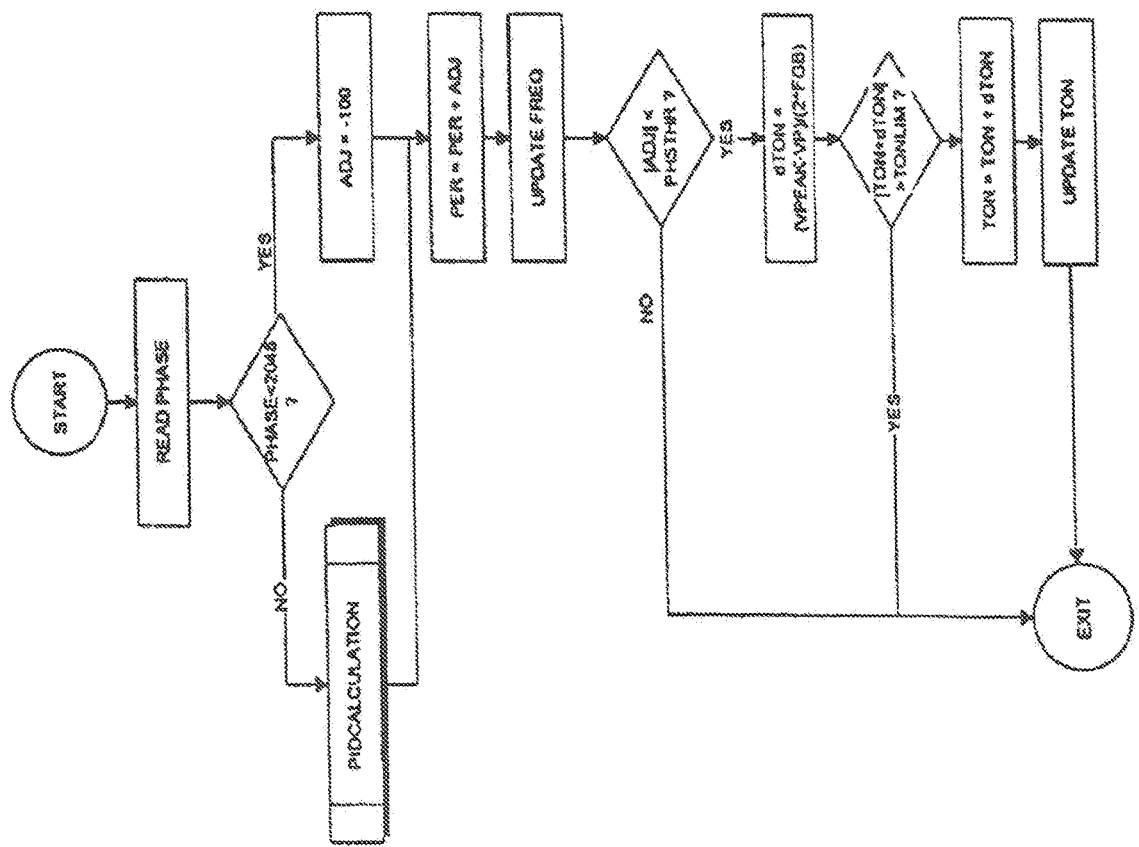
FIG. 9 is another flow chart of the program in the microprocessor of FIG. 1 which provides the resonant scanner service routine.

FIG. 9 shows the DOFLEX routine, which is responsible for calculating the resonant scanner (flexure) operating frequency and updating the FREQ and TON registers shown in FIG. 2. DOFLEX first retrieves the phase measurement from the phase measurement circuit shown in FIG. 4. The measured phase value is compared to a noise threshold, 2048, which prevents the system from processing artificially low values that are probably due to resonant scanner drive induced current transients. Assuming the measured phase is larger than 2,047, it is considered valid and is further processed by a PID filter.

If the measured phase is too small for valid consideration (e.g., <2048), the resonant scanner's drive frequency is too far from its natural frequency to induce detectable mirror movement. Because the initial operating frequency is established to be the scanner's maximum resonant frequency plus 15%, the drive frequency will be higher than desired the firmware program correspondingly reduces the operating frequency by a fixed amount, preferably 100 counts. In doing so, the program effectively hunts for an operating frequency that is close to, but higher than the resonant scanner's actual natural frequency. Eventually, the drive frequency will be reduced to a frequency that is close enough to the scanner's natural frequency than the scanner's movement will be detectable resulting in valid phase measurements.

Figure 11:
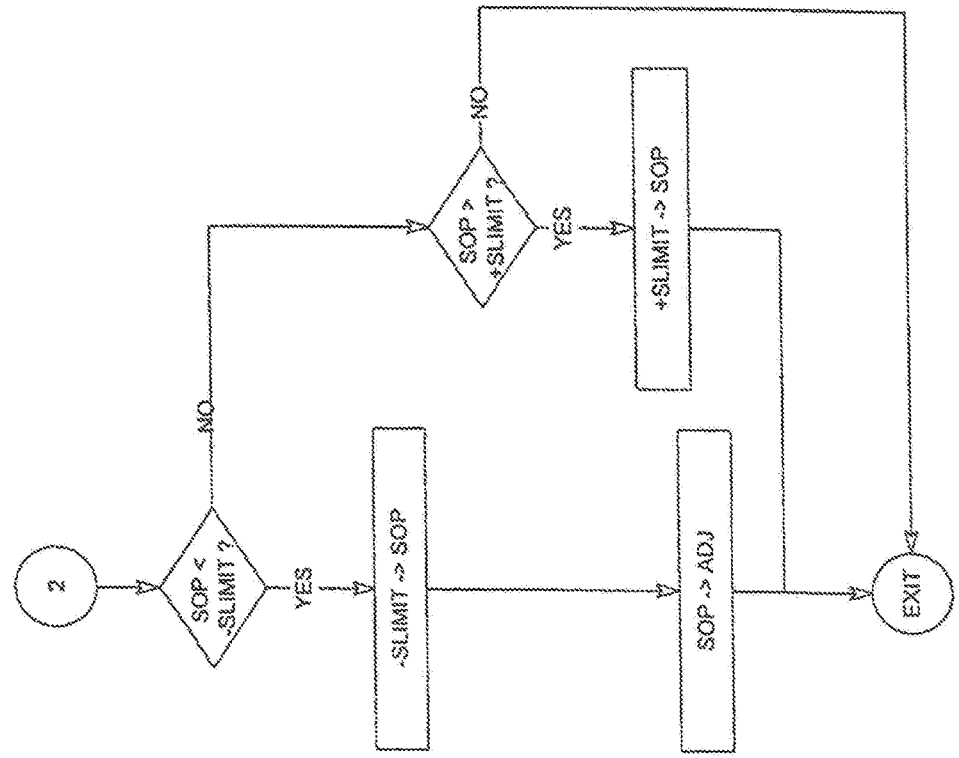
FIGS. 10 and 11 are flow charts showing how programming in the microprocessor implements the PID calculation.
Figure 10:
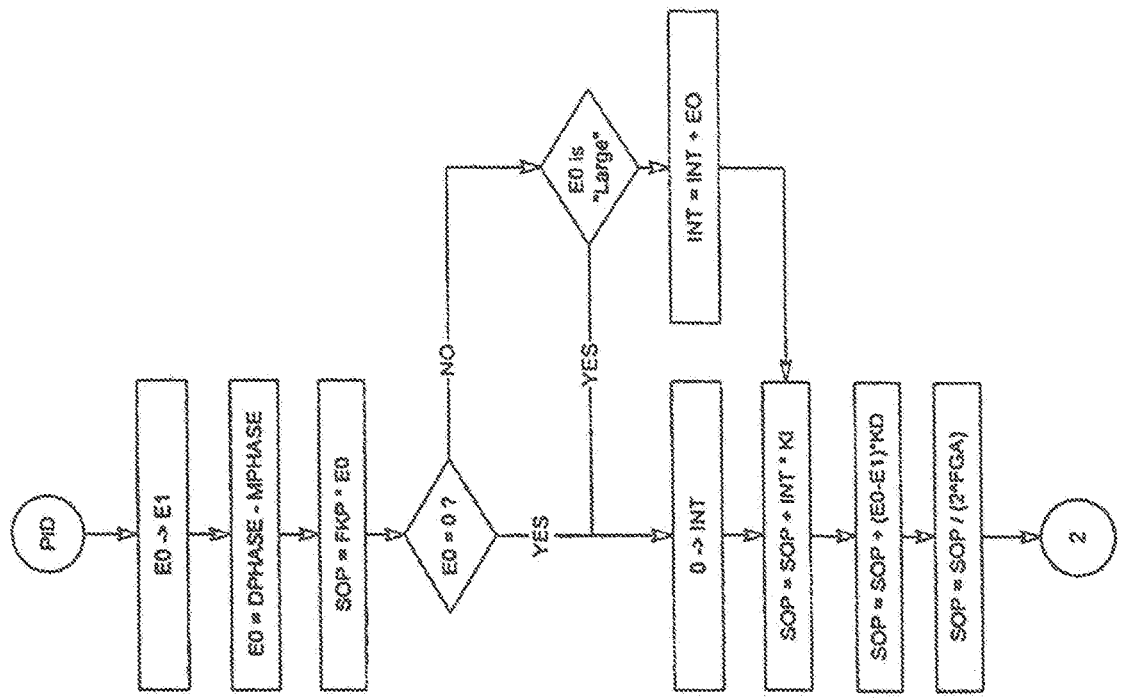

Assuming valid (>2047 count) phase measurements are detected, these measurements are input to a proportional control loop for further frequency refinement. The PID CALCULATION shown in FIG. 10 and FIG. 11 is invoked. These figures show how successive measured phase values are numerically processed by a classic digital proportional-derivative-integral filter to obtain a new value for ADJ, the amount the flexure operating frequency will be adjusted by to obtain stable oscillation. DPHASE is nominally 5600. FKP is 800, KD is 200 and KI is 20. FGA is 15.

The bottom portion of FIG. 9 implements the secondary control loop to maintain constant scan angle. The first, frequency, control loop has locked and is stable during scan angle control. This is accomplished by comparing the frequency adjustment factor, ADJ, with a predefined threshold value, preferably 3. When ADJ is less than 3, the frequency control loop is considered locked and stable, and amplitude (scan angle) control becomes active.

As mentioned earlier, scan angle is controlled by adjusting the TON register which effectively controls the scanner's drive pulse width (in FIG. 2). The variable dTON is computed based on the simple algebraic difference between the aforementioned 32 summed peak values, stored in VP, and 32 times the desired peak value of ANGLE, corresponding to the highest peak voltage available at the input of VCO 14, corresponding to 4.5 volts. This value is 6,720 or 32*210.

Stated in another way, the resonant scanner control system utilizes a dual-variable control loop maintains a constant scan angle as measured by a peak detector examining an offset version of POSITION signal derived from the resonant scanner's monitored VELOCITY signal. Further, that the resonant scanner is operated at, or very near, its resonant frequency by monitoring the motion that results from the applied drive frequency and adjusting said frequency so that the resulting motion lags the drive waveform by 90°, thus insuring the system operates at resonance.

From the foregoing description, it will be apparent that an improved hand held confocal scanning laser microscope has been provided and also a resonant scanner control system especially adapted for use therein. Variations and modifications in the herein described microscope and its optical and electrical systems, within the scope of the invention, will undoubtedly become apparent to those skilled in the art. According the foregoing description should be taken as illustrative and not in a limiting sense.

The invention claimed is:

1. An optical assembly for imaging a section of a specimen by illuminating said section with a scanning beam and receiving returned light from said section, said optical assembly comprising:
   an objective via which said scanning beam is incident on said specimen and on which said return beam is incident, wherein said objective has an entrance aperture defining an entrance pupil;
   oscillating mirrors which translate an illumination beam into said scanning beam and receives said return beam for descanning said return beam which is then focused onto a detector to provide signals representative of one or more images of a section on or within said specimen, in which said oscillating mirrors repeatedly scan a field of view; and
   a telescope having multiple lenses, said entrance pupil of said objective being imaged between said oscillating mirrors by said telescope, wherein one of said oscillating mirrors has a scan angle, and said scan angle is varied to change zoom of said one or more images while maintaining position of the lenses of said telescope with respect to each other, wherein said lenses of said telescope are disposed between said objective and a nearest one of said mirrors to said objective, and said lenses of said telescope comprises at least a first of said lenses being closest to said mirrors and a second of said lenses being closest to said objective, said first and said second of said lenses each having a focal length, in which said focal length of said first of said lenses is less than said focal length of said second of said lenses, and said focal length of said first of said lenses and said focal length of said second of said lenses being in a ratio to provide magnification to enable filling of said entrance pupil across an entire length of said scanning beam.

2. The optical assembly according to claim 1 wherein said one of said mirrors is part of a resonant scanner, and said scan angle is varied by adjustment of said resonant scanner.

3. The optical assembly according to claim 1 wherein said telescope has a magnification sufficient to fill said entrance pupil entirely during scanning to compensate for the distance that the scanning beam walks over said entrance pupil during scanning to maintain the numerical aperture (NA) of said objective constant over said scan.

4. The optical assembly according to claim 1 wherein said first of said lenses has a focal point midway between said mirrors.

5. The optical assembly according to claim 1 further comprising a pinhole, and said return beam is focused via said pinhole onto said detector to provide said signals representative of one or more images of said section within said specimen.

6. The optical assembly according to claim 1 wherein said objective has an optical axis coincident with said optical axis of said telescope.

7. The optical assembly according to claim 1 wherein said oscillating mirrors represent a pair of oscillating mirrors which are in a spaced relationship with each other to minimize spacing between said mirrors without mechanical interference with oscillation of said mirrors.

8. The optical assembly according to claim 7 wherein said spacing between said mirrors provides clearance between said mirrors which prevents said interference during the oscillation thereof.

9. The optical assembly according to claim 1 wherein said telescope has a magnification sufficient to overfill said entrance pupil with said illumination beam such that said entrance pupil is filled with said illumination beam over a full deflection of said scanning beam over said entrance pupil.

10. The optical assembly according to claim 2 further comprising a frequency and scan angle control system for providing drive pulses at a rate which drives said resonant scanner.

11. The optical assembly according to claim 10 wherein said resonant scanner has a drive input receiving said drive pulses and a sense output providing an input to said control system, and said control system changes the scan angle of said one of said mirrors by varying a duration of said drive pulses.

12. An optical assembly for imaging a section of a specimen by illuminating said section with a scanning beam and receiving returned light from said section, said optical assembly comprising:
an objective via which said scanning beam is incident on said specimen and on which said return beam is incident, wherein said objective has an entrance aperture defining an entrance pupil;
oscillating mirrors which translate an illumination beam into said scanning beam and receives said return beam for descanning said return beam which is then focused onto a detector to provide signals representative of one or more images of a section on or within said specimen, in which said oscillating mirrors repeatedly scan a field of view;
a telescope having multiple lenses disposed for passing said scanning beam to said objective and passing said return beam from said objective to said oscillating mirrors, said entrance pupil of said objective being imaged between said oscillating mirrors by said telescope, wherein one of said oscillating mirrors has a scan angle, said scan angle is varied to change zoom of said one or more images while maintaining position of the lenses of said telescope with respect to each other, said one of said mirrors is part of a resonant scanner, and said scan angle is varied by adjustment of said resonant scanner; and
a frequency and scan angle control system for providing drive pulses at a rate which drives said resonant scanner, wherein said resonant scanner has a drive input receiving said drive pulses and a sense output providing an input to said control system, and said control system changes the deflection angle of said one of said mirrors by varying an amplitude of said drive pulses.

13. An optical assembly for imaging a section of a specimen by illuminating said section with a scanning beam and receiving returned light from said section, said optical assembly comprising:
an objective via which said scanning beam is incident on said specimen and on which said return beam is incident, wherein said objective has an entrance aperture defining an entrance pupil;
oscillating mirrors which translate an illumination beam into said scanning beam and receives said return beam for descanning said return beam which is then focused onto a detector to provide signals representative of one or more images of a section on or within said specimen, in which said oscillating mirrors repeatedly scan a field of view;
a telescope having multiple lenses disposed for passing said scanning beam to said objective and passing said return beam from said objective to said oscillating mirrors, said entrance pupil of said objective being imaged between said oscillating mirrors by said telescope, wherein one of said oscillating mirrors has a scan angle, said scan angle is varied to change zoom of said one or more images while maintaining position of the lenses of said telescope with respect to each other, said one of said mirrors is part of a resonant scanner, and said scan angle is varied by adjustment of said resonant scanner; and
a frequency and scan angle control system for providing drive pulses at a rate which drives said resonant scanner, wherein said control system provides said drive pulses of opposite polarity which drive said one of said mirrors in opposite directions during each half cycle of oscillation of said one of said mirrors, and means for providing a video signal for successive lines of an image from scans in each of said opposite directions.

14. A method for imaging a section of a specimen by illuminating said section with a scanning beam and receiving returned light from said section, said method comprising steps of:
providing an objective via which said scanning beam is incident on said specimen and on which said return beam is incident, wherein said objective has an entrance aperture defining an entrance pupil;
oscillating mirrors to translate an illumination beam into said scanning beam and receive said return beam for descanning said return beam, wherein one of said oscillating mirrors has a scan angle;
focusing said return beam onto a detector to provide signals representative of one or more images of a section on or within said specimen, in which said oscillating of said oscillating mirrors repeatedly scan a field of view;

imaging said entrance pupil of said objective between said oscillating mirrors using a telescope having multiple lenses disposed between said objective and a nearest one of said mirrors to said objective with at least a first of said lenses being closest to said mirrors and a second of said lenses being closest to said objective, said first and said second of said lenses each having a focal length in which said focal length of said first of said lenses is less than said focal length of said second of said lenses, and said focal length of said first of said lenses and said focal length of said second of said lenses being in a ratio to provide magnification to enable filling of said entrance pupil across an entire length of said scanning beam; and varying said scan angle of said one of said oscillating mirrors to change zoom of said one or more images while maintaining position of the lenses of said telescope with respect to each other.

15. The method according to claim 14 wherein said imaging step further comprises providing magnification with said telescope sufficient to fill said entrance pupil entirely during scanning to compensate for the distance that the scanning beam walks over said entrance pupil during scanning to maintain the numerical aperture (NA) of said objective constant over said scan.

16. The method according to claim 14 wherein said imaging step further comprises providing said magnification with said telescope to overfill said entrance pupil with said illumination beam such that said entrance pupil is filled with said illumination beam over a full deflection of said scanning beam over said entrance pupil.

17. The method according to claim 14 wherein said focusing step further comprises a step of focusing said return beam via a pinhole onto said detector to provide said signals representative of one or more images of said section within said specimen.

18. The method according to claim 14 wherein said oscillating step further comprises positioning a pair of mirrors, which oscillate to translate said illumination beam into said scanning beam, in a spaced relationship with each other to minimize spacing between said pair of mirrors without mechanical interference with each other when oscillating.

* * * * *